United States Patent
Mercolino et al.

(10) Patent No.: US 9,428,792 B2
(45) Date of Patent: Aug. 30, 2016

(54) NUCLEIC ACID-BASED AUTHENTICATION AND IDENTIFICATION CODES

(71) Applicant: CertiRx Corporation, Research Triangle Park, NC (US)

(72) Inventors: Thomas J. Mercolino, Chapel Hill, NC (US); Amy McPherson, Raleigh, NC (US); James Garber Rudulph, Jr., Durham, NC (US)

(73) Assignee: CertiRx Corporation, Research Triangle Park, NC (US)

(*) Notice: Subject to any disclaimer, the term of this patent is extended or adjusted under 35 U.S.C. 154(b) by 117 days.

(21) Appl. No.: 14/211,965

(22) Filed: Mar. 14, 2014

(65) Prior Publication Data

US 2014/0272973 A1    Sep. 18, 2014

Related U.S. Application Data

(60) Provisional application No. 61/783,991, filed on Mar. 14, 2013.

(51) Int. Cl.
 *C07H 21/04* (2006.01)
 *C12Q 1/68* (2006.01)

(52) U.S. Cl.
 CPC .................................. *C12Q 1/68* (2013.01)

(58) Field of Classification Search
 None
 See application file for complete search history.

(56) References Cited

U.S. PATENT DOCUMENTS

| | | | |
|---|---|---|---|
| 4,713,326 A | 12/1987 | Dattagupta | |
| 4,997,772 A | 3/1991 | Sutton | |
| 5,049,490 A | 9/1991 | Sutherland | |
| 5,139,812 A | 8/1992 | Lebacq | |
| 5,147,777 A | 9/1992 | Sutton | |
| 5,149,737 A | 9/1992 | Ponticello | |
| 5,177,023 A | 1/1993 | Sutton | |
| 5,210,289 A | 5/1993 | Ponticello | |
| 5,278,267 A | 1/1994 | Ponticello | |
| 5,451,505 A | 9/1995 | Dollinger | |
| 5,563,037 A | 10/1996 | Sutherland | |
| 6,159,504 A | 12/2000 | Kumabe | |
| 6,235,473 B1 | 5/2001 | Friedman | |
| 6,632,526 B1 | 10/2003 | Chandler | |
| 6,649,414 B1 | 11/2003 | Chandler | |
| 6,773,812 B2 | 8/2004 | Chandler | |
| 6,919,009 B2 | 7/2005 | Stonas | |
| 7,874,489 B2 * | 1/2011 | Mercolino | G01N 21/643 235/491 |
| 8,247,018 B2 * | 8/2012 | Mercolino | G01N 21/643 215/232 |
| 2003/0064105 A1 | 4/2003 | Kim | |
| 2003/0186257 A1 * | 10/2003 | Bertling | C12Q 1/68 435/6.16 |
| 2004/0219287 A1 | 11/2004 | Regan et al. | |
| 2005/0008762 A1 | 1/2005 | Sheu | |
| 2005/0037439 A1 | 2/2005 | Bourner et al. | |
| 2005/0112610 A1 | 5/2005 | Lee et al. | |
| 2006/0054506 A1 | 3/2006 | Natan | |
| 2007/0012784 A1 | 1/2007 | Mercolino | |
| 2007/0048761 A1 * | 3/2007 | Reep | C09D 7/1233 435/6.11 |
| 2008/0299559 A1 | 12/2008 | Kwok et al. | |
| 2011/0190920 A1 | 8/2011 | Mercolino | |
| 2013/0244894 A1 * | 9/2013 | Mercolino | C12Q 1/6834 506/9 |
| 2014/0031538 A1 * | 1/2014 | Chow | C12N 15/1034 536/25.3 |

FOREIGN PATENT DOCUMENTS

| | | |
|---|---|---|
| JP | 06298650 A | 10/1994 |
| WO | 0146474 A1 | 6/2001 |
| WO | 2013143014 A1 | 10/2013 |

OTHER PUBLICATIONS

IPRP for Application No. PCT/US2014/27718 dated Oct. 10, 2014.
Authentiform Technologies, LLC et al, International Application No. PCT/US2013/030435, International Search Report and Written Opinion, May 27, 2013.
Eth Zurich, Nanotechnology Protects Olive Oil from Counterfeiters, Nanowerk News, Apr. 24, 2014, http://www.nanowerk.com/nanotechnology_news/newsid=35317.php.

* cited by examiner

*Primary Examiner* — Jeanine A Goldberg
(74) *Attorney, Agent, or Firm* — NK Patent Law, PLLC

(57) ABSTRACT

The present disclosure relates to nucleic-acid based product authentication and identification by determining authentication codes comprising target nucleic acids using oligonucleotide probes associated with samples. The presence of the authentication code is determined using detection methods, such as flow cytometric methods, capable of particle discrimination based on the light scattering or fluorescence properties of the particle. Target-correlated fluorescence signal, originating from a target nucleic acid hybridized to labeled complementary oligonucleotides is determined as an indicator of the presence of the authentication code. In some embodiments, an intercalating dye is used to determine the presence of target nucleotide/oligonucleotide heterodimers and identify an authentication code.

14 Claims, 13 Drawing Sheets

```
                        SEQUENCE LISTING

<160> NUMBER OF SEQ ID NOS: 16

<210> SEQ ID NO 1
<211> LENGTH: 90
<212> TYPE: DNA
<213> ORGANISM: Artificial Sequence
<220> FEATURE:
<223> OTHER INFORMATION: Synthetic Construct

<400> SEQUENCE: 1
tttccaagta agcaataacg tcagctcttt cttgtggctt cttcatacca gcgaaagaca      60
tcttagtacc tggcatgaac ttctttgggt                                        90

<210> SEQ ID NO 2
<211> LENGTH: 87
<212> TYPE: DNA
<213> ORGANISM: Artificial Sequence
<220> FEATURE:
<223> OTHER INFORMATION: Synthetic Construct

<400> SEQUENCE: 2
acccaaagaa gttcatgcca ggtactaaga tgtctttcgc tggtatgaag aagccacaag      60
aaagagctga cgttattgct ttggaaa                                           87

<210> SEQ ID NO 3
<211> LENGTH: 166
<212> TYPE: DNA
<213> ORGANISM: Artificial Sequence
<220> FEATURE:
<223> OTHER INFORMATION: Synthetic Construct

<400> SEQUENCE: 3
ctgcaggcgc cagcgtggac catcaagtag taatgaacgc acggacgagg acatcataga      60
gattacacct ttatccacag ttctcggtct aacgcagcag tcagtgtatc agcaccagca     120
tccgtagtga gtcttcagtg tctgctccag gatcgtggcg ctgcag                    166
```

```
<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4
cgccagcgtg gaccatcaag tagtaa                                          26

<210> SEQ ID NO 5
<211> LENGTH: 26
<212> TYPE: DNA
<213> ORGANISM: Artificial Sequence
<220> FEATURE:
<223> OTHER INFORMATION: Synthetic Construct

<400> SEQUENCE: 5
cacgatcctg gagcagacac tgaaga                                          26

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
ctgcgttaga ccgagaactg tggataaagg                                      30

<210> SEQ ID NO 7
<211> LENGTH: 35
<212> TYPE: DNA
<213> ORGANISM: Artificial Sequence
<220> FEATURE:
<223> OTHER INFORMATION: Synthetic Construct

<400> SEQUENCE: 7
ttaaataggt atcgcgtgct tactccggtg gaccg                                35

<210> SEQ ID NO 8
<211> LENGTH: 35
<212> TYPE: DNA
<213> ORGANISM: Artificial Sequence
<220> FEATURE:
<223> OTHER INFORMATION: Synthetic Construct

<400> SEQUENCE: 8
tcgcacttat ctcgtaccgt gaacacctag cgcgt                                35

<210> SEQ ID NO 9
<211> LENGTH: 35
<212> TYPE: DNA
<213> ORGANISM: Artificial Sequence
<220> FEATURE:
<223> OTHER INFORMATION: Synthetic Construct

<400> SEQUENCE: 9
gatcgacgta catgcccgat ccacggacat tcttt                                35

<210> SEQ ID NO 10
<211> LENGTH: 35
<212> TYPE: DNA
<213> ORGANISM: Artificial Sequence
<220> FEATURE:
<223> OTHER INFORMATION: Synthetic Construct
```

<400> SEQUENCE: 10
acgatcacgc gtgcaattgg tacacgagcc gagtc                                35

<210> SEQ ID NO 11
<211> LENGTH: 51
<212> TYPE: DNA
<213> ORGANISM: Artificial Sequence
<220> FEATURE:
<223> OTHER INFORMATION: Synthetic Construct

<400> SEQUENCE: 11
actagatacc cagcacgcct tggacgcgac atatctcacc cctggagcgg c              51

<210> SEQ ID NO 12
<211> LENGTH: 51
<212> TYPE: DNA
<213> ORGANISM: Artificial Sequence
<220> FEATURE:
<223> OTHER INFORMATION: Synthetic Construct

<400> SEQUENCE: 12
gagctcacag ttcctaaagt gtaatggccg gctacgctaa gcgcattgat t              51

<210> SEQ ID NO 13
<211> LENGTH: 51
<212> TYPE: DNA
<213> ORGANISM: Artificial Sequence
<220> FEATURE:
<223> OTHER INFORMATION: Synthetic Construct

<400> SEQUENCE: 13
caacgtgagc tcttatcact cctatctgat tccctatcga tacatgccag g              51

<210> SEQ ID NO 14
<211> LENGTH: 51
<212> TYPE: DNA
<213> ORGANISM: Artificial Sequence
<220> FEATURE:
<223> OTHER INFORMATION: Synthetic Construct

<400> SEQUENCE: 14
gtcataagta tactcctcac acggagtcgc cacacctatg aagagtagtg t              51

<210> SEQ ID NO 15
<211> LENGTH: 51
<212> TYPE: DNA
<213> ORGANISM: Artificial Sequence
<220> FEATURE:
<223> OTHER INFORMATION: Synthetic Construct

<400> SEQUENCE: 15
ggtagcacta gttgctccga gagggtctat tgcggccgca gccggccata t              51

<210> SEQ ID NO 16
<211> LENGTH: 51
<212> TYPE: DNA
<213> ORGANISM: Artificial Sequence
<220> FEATURE:
<223> OTHER INFORMATION: Synthetic Construct

<400> SEQUENCE: 16
gttgtcgttg cgcctgaatc tcgtataaga tatacagggt gatcgacggc t              51

NUCLEIC ACID-BASED AUTHENTICATION AND IDENTIFICATION CODES

CROSS-REFERENCE TO RELATED APPLICATIONS

This application claims the benefit of U.S. provisional patent application No. 61/783,991, filed Mar. 14, 2013, the disclosure of which is hereby incorporated by reference in its entirety.

TECHNICAL FIELD

The presently disclosed subject matter is directed to nucleic acid based product authentication by determining the presence of target nucleic acids. In particular, the present disclosure provides methods for simplifying the detection process so that the authenticating nucleic acid can be detected in situ in the formulation of the product, on the surface of a product, or on product packaging, without sequencing. It also provides methods for achieving higher complexity, and hence more tamperproof, authentication codes comprising a combination of nucleic acids and taggants and marking locations in relatively small sets to allow for relatively large numbers of unique codes. The present disclosure further provides for using nucleic acids as identification means for linking contents to their original containers and corresponding information systems, for example as is useful for linking specimens to corresponding patient identification information.

BACKGROUND

Counterfeit items continue to pose a significant and growing problem with consumer packaged goods, especially for established brands. Because of their intrinsic capability to carry diverse coded information, nucleic acids have been used to provide a secure, cost effective and forensic method to help companies protect their intellectual property and brand. Typically, nucleic acids are applied to the commercial article by means that stabilize it to manufacturing processes, then the nucleic acid can be sequenced to verify the product's authenticity. Unique nucleic sequences must be synthesized for each coding identifier.

Linking identification of specimen container contents to patient identification is a critical unmet need in clinical lab diagnostics. Because of their intrinsic capability to carry diverse coded information and their innate and nearly ubiquitous presence in biological specimens, nucleic acids have been used to provide a secure forensic method to help diagnosticians ensure that sample identification is correct. Typically, a biological specimen with an identity in question may be matched to an individual's identity if the DNA that occurs naturally in the specimen and the DNA from a sample known to come from the individual are sequenced and matched. This process offers identification at a high level of certainty, but typically at high costs in terms of expense, effort, and time.

Likewise, microparticulate taggants have been used as means for authenticating products. For example, U.S. Pat. No. 7,874,489 disclosed using such taggants, combining taggants that have different detectable physical properties, wherein each combination of properties is used as an encoding bit to create codes. Similarly to nucleic acids, unique taggants with unique combinations of physical properties must be manufactured in order to increase the number and complexity of possible codes.

The detection of nucleic acids is widely employed for determining the presence and copy number of specific genes and known sequences. An important characteristic of nucleic acids is their ability to form sequence-specific hydrogen bonds with a nucleic acid having a complementary nucleotide sequence. This ability of nucleic acids to hybridize to complementary strands of nucleic acids has been used to advantage in what are known as hybridization assays, and in DNA purification techniques. In a hybridization assay, a nucleic acid having a known sequence is used as a probe that hybridizes to a target nucleic acid having a complementary nucleic acid sequence. Labeling the probe allows detection of the hybrid and, correspondingly, the target nucleic acid.

Because of their intrinsic capability to carry diverse coded information, nucleic acids have been used to provide a secure, cost effective and forensic method to help companies protect their intellectual property and brand. U.S. Pat. No. 5,139,812 discloses the use of nucleic acid sequences in ink for identifying an object with a probe. U.S. Pat. No. 5,451,505 uses nucleic acids as taggants. Such techniques also are not readily perceptible without the aid of special equipment, which develop the presence of such markers. U.S. Patent Application Publication No. 2005/0112610 discloses the use of nucleic acid sequences for identifying textiles. However, for each unique code it is required that a separate, unique target nucleic acid sequence be synthesized, increasing cost and decreasing practicality of the methods. Moreover, complex and expensive sequencing analysis has typically been required to identify such unique sequences.

The presently disclosed subject matter overcomes certain of the above limitations in Identif's Bio-Molecular Marker Covert system, which is based on a synthetic target nucleic acid sequence supplied as an ink. The Indentif product's label is imprinted with a customer-specific ink, which can be identified in the field by activating the marking with a pen that contains the mating strand. One of the half strands of DNA is accompanied by a "molecular beacon" fluorophore. When unmatched, the fluorophore is not visible. But when matched with a mating strand, it opens and the fluorophore becomes detectable. In contrast to Identif's technology, the signal in the presently disclosed subject matter does not require that either strand be synthesized with costly molecular beacon technology incorporated. Additionally, the methods of the present disclosure do not require synthesis of separate, unique target nucleic acid sequences for each customer-specific code, as is the case with Identif's method.

Applied DNA Sciences offers the SigNature™ Program based on APDN's plant-derived DNA sequences. Botanical DNA is encrypted into inks, paper, thread, holograms and other mediums, or printed in a botanical DNA SigNature logo that highlights the word "Nature". The logo has been designed to contain embedded botanical DNA, for overt detection and forensic authentication purposes. For real-time detection, APDN offers a proprietary SigNature DNA detection pen that is applied over the DNA-embedded SigNature logo, prompting a reversible color change. No details have been uncovered relating to the chemistry of detection, but the APDN method is subject to the same limitations as those identified for Identif's.

Thus, there is an unmet need for more tamperproof authentication technology that is also cost effective. The present disclosure provides such improved authentication technology.

SUMMARY

In one aspect, the present disclosure relates to a method for authenticating a product by determining the presence of a target nucleic acid in the formulation of the product, on the surface of a product, or on the product packaging, comprising the steps of:

a) associating an authentication code comprising the target nucleic acid with the article to be authenticated; b) contacting the article with an oligonucleotide probe comprising a nucleic acid sequence complementary to at least a portion of the target nucleic acid; and c) determining the presence of the authentication code by contacting the duplex heterodimer formed by said target nucleic acid and oligonucleotide probe to a reporter compound which is capable of binding to duplex nucleic acid and which upon binding or being bound thereto is capable of producing a detectable signal. Association may be achieved preferably by immobilization within the formulation of a solid product (e.g., paper), on the surface of a product, or on product packaging Optionally, steps b and c are performed sequentially, or preferably, at the same time. A detectable signal, or signal change correlates to immobilized target hybridized to oligonucleotide probe and is thereby an authentication signal. The methods of this embodiment are particularly well suited to detection of the target nucleic acid with a pen that contains both oligonucleotide probe and an intercalating dye. The requirement for detector oligonucleotide, that is, the oligonucleotide probe to match target nucleic acid provides for "lock & key" assurance.

In one embodiment, the method includes an authentication pouch comprising the authentication which comprises the target nucleic acid(s) and/or microparticles having distinctly measurable properties. In another embodiment, the target nucleic acid(s) are intrinsic to a pharmaceutical formulation, including where such intrinsic nucleic acid is the active pharmaceutical ingredient.

In another aspect, the present disclosure relates to a method for authenticating a product by determining the presence of an authentication code comprising at least two target nucleic acid sequences and comprising the steps of: a) immobilizing each target nucleic acid to the product to be authenticated at a discernable location on the article; b) contacting said locations with at least two oligonucleotide probes each comprising nucleic acid sequences complementary to at least a portion of one of the target nucleic acids, and c) determining the presence of the authentication code by contacting the duplex heterodimer formed by said target nucleic acids and oligonucleotide probes to a reporter compound which is capable of binding to duplex nucleic acid and which upon binding or being bound thereto is capable of producing a detectable signal.

Optionally, steps b and c are performed sequentially, or preferably, at the same time. Optionally, immobilization is performed in a specified morphology or symbology wherein revealing the presence of the target oligonucleotide also reveals a specific shape or symbol and/or size at each location. A detectable signal, or signal change at said discernable location correlates to immobilized target hybridized to oligonucleotide probe. Combining location with morphology and size allows very few unique target nucleic acid sequences to be synthesized in order to achieve very high complexity codes. For example, selecting 2 of the characters A-Z and numbers 0-9 (36 possibilities) for each of two locations, and printing each location with either of 2 possible target nucleic acid sequences and in 3 possible discernable sizes yields 7776 possible codes from just these two sequences. Again, the methods of this embodiment are equally well suited to detection with a pen system and provides for "lock & key" assurance, as above.

In another embodiment of the present disclosure, the method for authenticating an article or product by determining the presence of a target nucleic acid comprises the steps of: a) immobilizing the target nucleic acid to a substrate, wherein the substrate is a particle that is capable of scattering electromagnetic radiation of wavelength greater than or equal to about 200 nm; or comprises a distinct first compound or plurality of compounds capable of producing a distinct fluorescence signal corresponding to the particle; or capable of said scattering and producing said fluorescence signal; b) associating said substrate with the article to be authenticated; c) contacting the substrate to an oligonucleotide probe comprising a nucleic acid sequence complementary to at least a portion of the target nucleic acid, and d) contacting the duplex heterodimer formed by said target nucleic acid and oligonucleotide probe to a reporter compound which is capable of binding to duplex nucleic acid and which upon binding or being bound thereto is capable of producing a detectable signal.

Optionally, steps c and d are performed sequentially, or preferably, at the same time. Optionally, the oligonucleotide of step c is covalently labeled with a reporter that generates a detectable signal, for example, a fluorescent moiety or a "molecular beacon", in which case step d is unnecessary. A detectable signal, or signal change that is correlated with the particles measured light scattering, distinct fluorescence signal, or the combination of light scatter and fluorescence indicates that immobilized target has hybridized to oligonucleotide probe and is thereby an authentication signal. In this example, combining particle light scattering and distinct fluorescence signal enables that very few unique target nucleic acid sequences need to be synthesized in order to achieve very high complexity codes. For example, selecting microparticle entities having two distinct light scatter signals, 2 colors of fluorescence, and 5 levels of fluorescence can be classified into 20 possible clusters. If either of two possible target nucleic acid sequences is used in conjunction with all possible combinations of these clusters, the number of possible codes is very large.

Optionally, the count or relative count of microparticles per cluster can be a component of the code, which results in extraordinarily large numbers of possible codes from small numbers of unique target nucleic acid sequences. Again, the methods of this embodiment provides for "lock & key" assurance, as above. Any particle analysis method or device capable of distinguishing particles from background and one target-specific particle from another by detecting particle-associated scattering and/or fluorescence, and which is capable of detecting target-correlated signal, can be used in the practice of this embodiment. Laser flow cytometric methods are preferred. Fluorescence microscopic methods and devices can also be employed. Laser scanning methods and devices also can be used, for example.

Any particle analysis method or device capable of distinguishing particles from background and one target-specific particle from another by detecting particle-associated scattering and/or fluorescence, and which is capable of detecting target-correlated signal, can be used in the practice of this presently disclosed subject matter. Laser flow cytometric methods are preferred. A laser flow cytometer useful in the practice of the present disclosure is the ORTHO CYTORONABSOLUTE® Flow Cytometer from Ortho-Clinical Diagnostics, Inc., Raritan, N.J. Fluorescence microscopic methods and devices can also be employed. Laser scanning methods and devices also can be used, for example, the Compucyte Laser Scanning Cytometer from Compucyte Corporation, Cambridge, Mass. Methods that permit spatial resolution of substrate-immobilized oligonucleotides can be used; laser scanning methods are particularly suitable. Methods and devices that are capable of distinguishing particles over background and resolving scattering or fluorescence signal from target-specific particles, and detecting target-correlated signal, as described above, that do not rely on physical separation of individual particles also can be employed.

In another aspect, the disclosure relates to product authentication using an authentication code comprising an amount of a plurality of distinct target nucleic acids, said method comprising:

A) forming a mixture, preferably in situ, comprising
  i) immobilized the target nucleic acids, and
  ii) target-specific particles, wherein a target-specific particle has immobilized thereto an oligonucleotide comprising a nucleic acid sequence complementary to at least a portion of one distinct target nucleic acid, wherein each particle independently is
    a) capable of scattering electromagnetic radiation of wavelength greater than or equal to about 200 nm, or
    b) comprises a distinct first compound or plurality of compounds capable of producing a distinct fluorescence signal corresponding to the particle, or
    c) capable of scattering electromagnetic radiation of wavelength greater than or equal to about 200 nm and comprises a distinct first compound or plurality of compounds capable of producing a distinct fluorescence signal corresponding to the distinct particle.

Additionally, the mixture, optionally, can be heated to denature duplex nucleic acid then cooled to allow hybridization of the target nucleic acid to the immobilized oligonucleotide or, if desired, the target nucleic acid can be heated prior to combination with immobilized oligonucleotide.

The method for determining multiple target nucleic acids, involves a step for producing a detectable signal, preferably an optical signal, most preferably fluorescence, correlated with target hybridized to immobilized oligonucleotide. A second compound capable of binding to duplex nucleic acid and producing a detectable fluorescence signal when bound thereto is combined with the mixture, or the oligonucleotide has linked thereto a second compound capable of fluorescence and the mixture is contacted with single-strand specific endonuclease, or the oligonucleotide or substrate comprises a second compound of fluorescence and the substrate or oligonucleotide comprises a fluorescence quenching compound in sufficient proximity to the second compound to quench fluorescence of the second compound prior to hybridization of target nucleic acid to immobilized oligonucleotide.

Using the above embodiments for producing a detectable signal correlated to target hybridized to immobilized probe, the mixture, in the case of particulate substrates, is exposed to, or introduced into a device or instrument, as described above, capable of detecting scattered electromagnetic radiation from a particle or upon detecting fluorescence from a first compound or plurality of compounds of a particle, or both, and detecting the fluorescence signal from the second compound as a measure of the presence of each distinct target nucleic acid. This can be accomplished because the target-specific particles can be distinguished by their specific light scattering and/or fluorescence. The second compound that provides target-correlated fluorescence signal, therefore, can be the same for each target. However, distinct second compounds for each target can be used if desired.

Fluorescence that may be associated with target nucleic acid and non-target nucleic acid free in solution, not hybridized to immobilized probe, does not contribute substantially, if at all, to the measured target-correlated signal.

In another aspect, the disclosure relates to a nucleic acid based product authentication kit wherein the product authentication code is encoded by a signature array of a population of particles associated with the product, wherein the signature array comprises information about the counts or relative counts of particles of at least two distinct clusters of particles within the population, comprising in the same or separate containers:

1) particles
  a) capable of scattering electromagnetic radiation of wavelength greater than or equal to about 200 nm, or
  b) comprising a compound or plurality of compounds capable of producing a fluorescence signal corresponding to the particle, or
  c) capable of scattering electromagnetic radiation of wavelength greater than or equal to about 200 nm and comprising a compound or plurality of compounds capable of producing a fluorescence signal corresponding to the particle;
2) an oligonucleotide comprising a nucleic acid sequence complementary to at least a portion of the target nucleic acid; and
3) a compound which is capable of binding to duplex nucleic acid and which upon binding or being bound thereto is capable of producing a detectable signal.

In another embodiment, the target nucleotide sequence or a plurality of target nucleic acid sequences that is or are intended for use in close association with biological organisms is designed so that they are dissimilar to known naturally occurring nucleotide sequences. In this embodiment, other aspects of the use of the target nucleotide sequence or a plurality of target nucleic acid sequences proceed as described above.

All of the above methods or kits can be configured for determining a single target nucleic acid or a plurality of target nucleic acids on a product to be authenticated. Further, the target nucleic acid and/or the microparticles comprising the authentication code may be contained in an authentication pouch associated with the product to be authenticated. As used herein, the term "immobilization" or "immobilized" means any means of spatially confining the subject nucleic acid, as may involve chemical, physical or physicochemical methods of immobilization.

DETAILED DESCRIPTION

Figure 1:
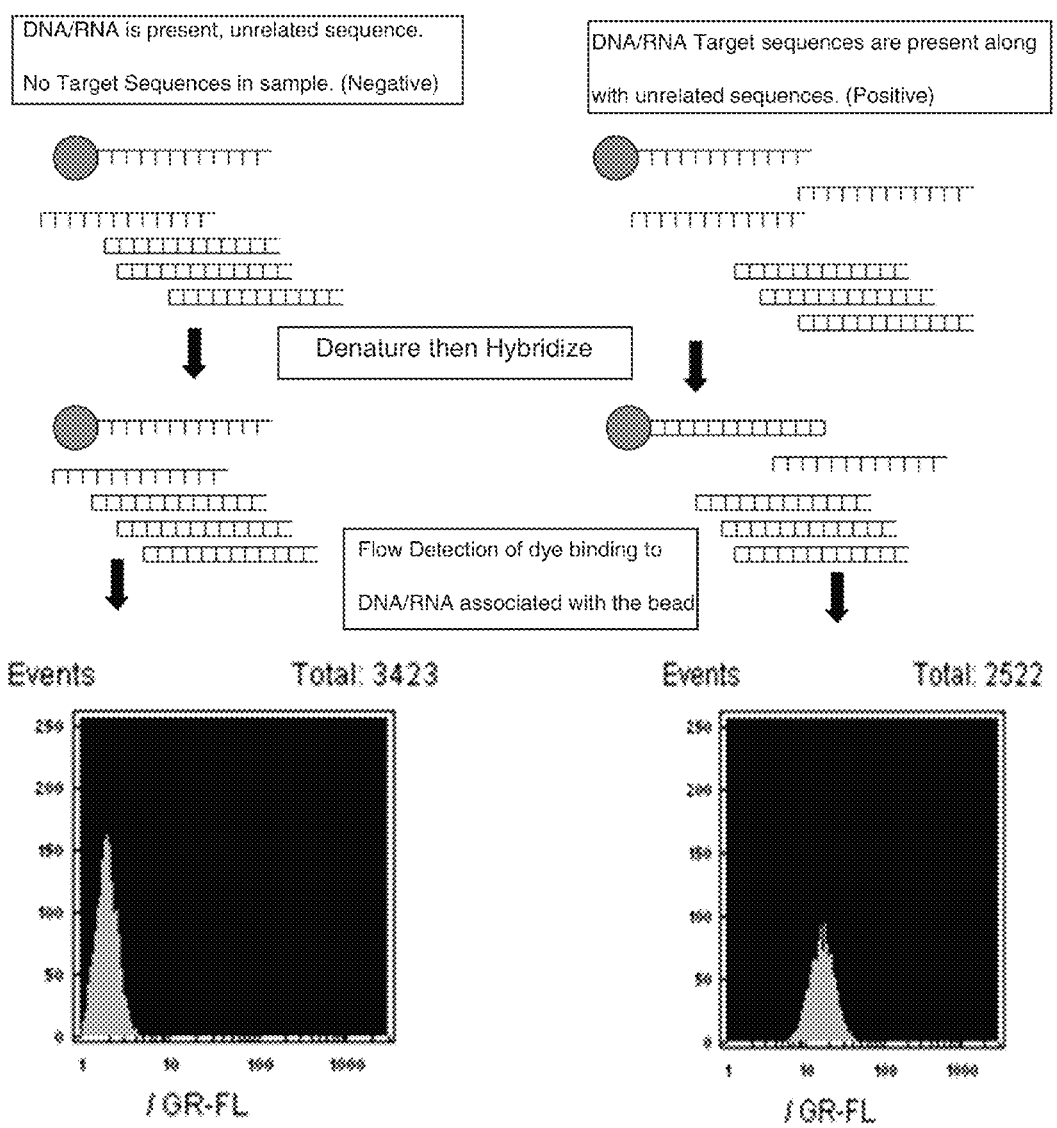
FIG. 1 is a schematic diagram depicting the hybridization and detection of target nucleic acid hybridized to particle-immobilized oligonucleotide.
Figure 2:
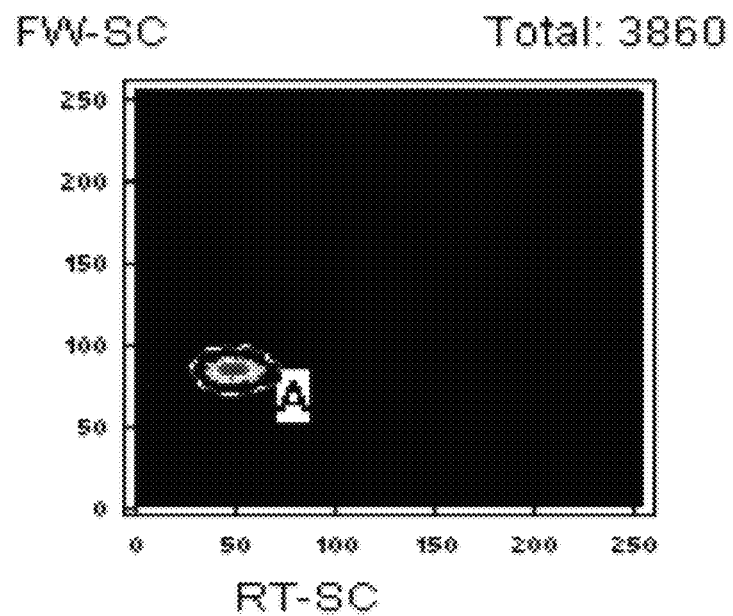
FIG. 2A is a plot of forward-angle vs right-angle light scattering (particle size selection) thiazole orange as target DNA indicator, in presence of CTDNA, target DNA was not present.
FIG. 2B is a plot of forward-angle vs right-angle light scattering (particle size selection), thiazole orange as target DNA indicator, 1000 femtomoles of target DNA in an excess of CTDNA.
FIG. 2C is a plot of forward-angle light scattering vs green fluorescence, thiazole orange as target DNA indicator in the presence of CTDNA, target DNA not present.
FIG. 2D is a plot of forward-angle light scattering vs green fluorescence, thiazole orange as target DNA indicator, 1000 femtomoles of target DNA in an excess of CTDNA.
FIG. 2E is a plot of the distribution of events vs green fluorescence, thiazole orange as target DNA indicator in the presence of CTDNA, target DNA not present.
FIG. 2F is a plot of the distribution of events vs green fluorescence, 1000 femtomoles of target DNA in an excess of CTDNA.
Figure 2B:
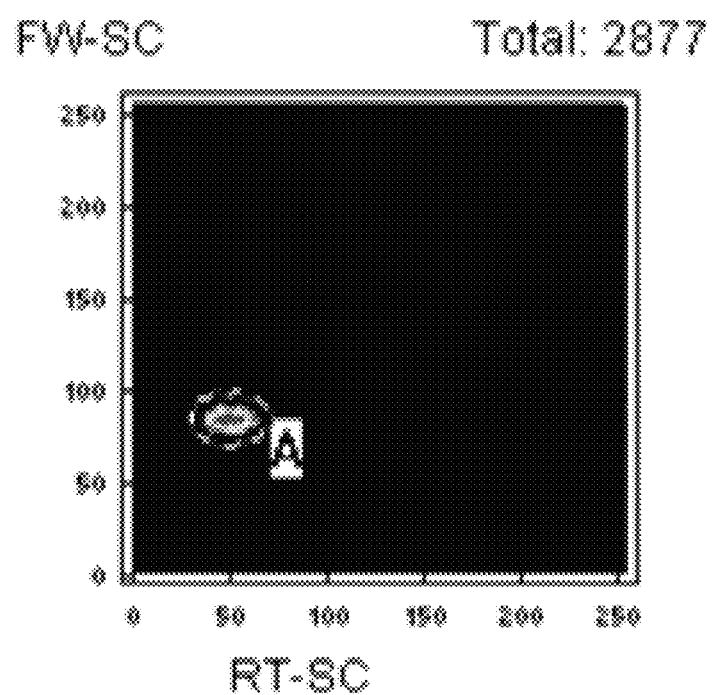
Figure 2C:
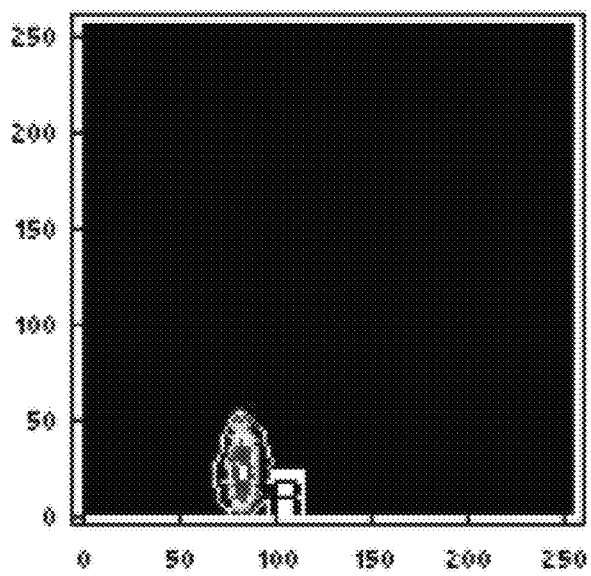
Figure 2D:
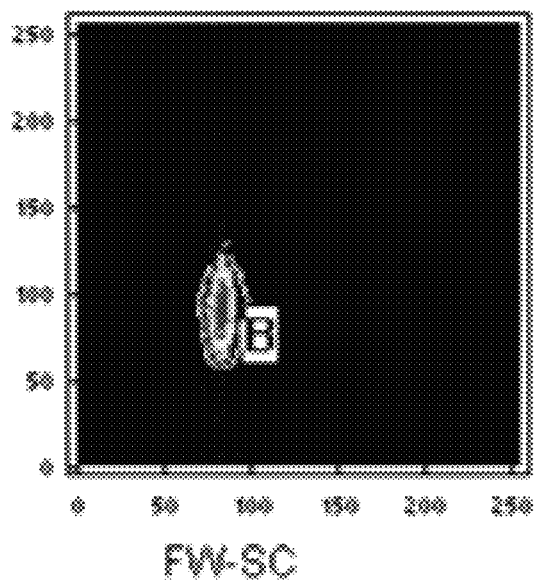
Figure 2E:
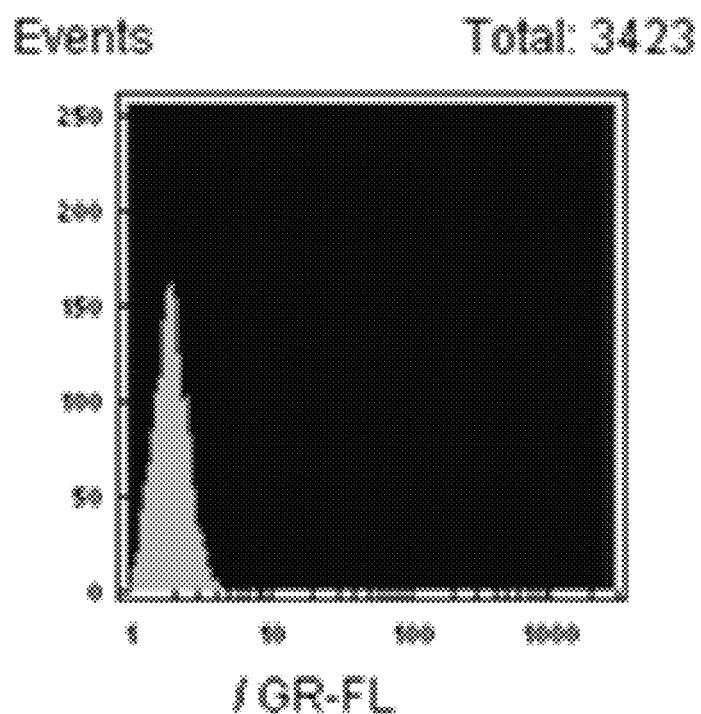
Figure 2F:
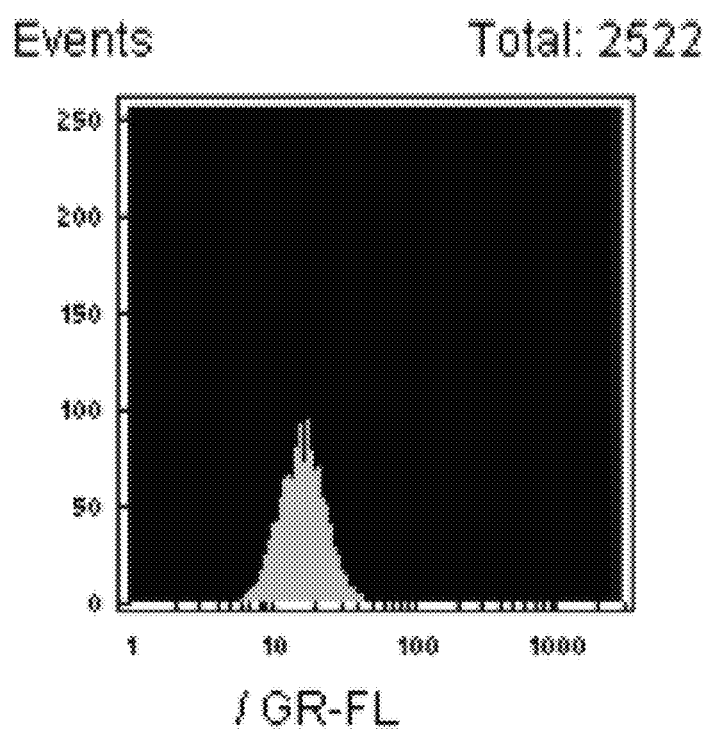

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

In one aspect, the presently disclosed subject matter describes methods for simplifying the detection process so that the authenticating nucleic acid can be detected in situ on the product without sequencing. It also provides methods to achieve higher complexity, and hence more tamperproof, authentication codes comprising a combination of nucleic acids and taggants and marking locations in relatively small sets to allow for relatively large numbers of unique codes. The requirement for detector oligonucleotide to match target nucleic acid provides for "lock & key" assurance.

Additional aspects of the presently disclosed subject matter include special design requirements for the nucleotide sequences in order to maximize their safety for use in products intended for intimate or parenteral contact with biological organisms, such as injectable pharmaceuticals, or ingested products, like certain pharmaceuticals, nutraceuticals, or foods.

All publications cited below are hereby incorporated by reference. Unless defined otherwise, all technical and scientific terms used herein will have the commonly understood meaning to one of ordinary skill in the art to which this present disclosure pertains.

It must be noted that as used herein and in the appended claims, the singular forms "a," "an," and "the" include plural reference unless the context clearly dictates otherwise. Thus, for example, a reference to "a population of entities" is a reference to one or more populations of entities and includes equivalents thereof known to those skilled in the art and so forth.

As used herein, the term "array" means a collection of data items arranged in such a way so that each data item in the array can be located.

As used herein, a "cluster of entities" or a "cluster" means a classification of at least two entities that are grouped together because they share one or more discretely measurable common properties. In particular embodiments of the present disclosure, the entities within "a cluster of entities" share one, two, three, four, five, six, seven, eight, nine, ten, or more discretely measurable common properties.

As used herein, the "count of entities per cluster", the "number of entities per cluster", the "count (or number) of entities within a cluster", and the "count (or number) of entities of a cluster" are used interchangeably to mean the number or sum total of entities within a cluster. The "count of entities per cluster" can be obtained by counting discrete entities within the cluster by means such as an automated counter or manual counting method.

As used herein, a "discretely measurable common property" is a property of or associated with each individual entity within a single cluster, and said property can be measured from the individual entity. The discretely measurable common property allows an entity to be assigned into a particular cluster. Entities having the same set of one or more discretely measurable common properties can be assigned into the same cluster. Entities having different sets of discretely measurable common properties can be assigned into distinct clusters.

Examples of "discretely measurable common property" include, but are not limited to, the properties of one or more tags associated with entities of a cluster, such as the fluorescent intensity or spectra when the entity is labeled with a fluorescent tag, the sizes of the entities, the shape of the entities, and other properties of the entities, such as being magnetic or not, density, or solid characterization, or the nucleotide sequence or amino acid sequence when the entities are composed of nucleic acid molecules or peptides/polypeptides.

As used herein, "distinct clusters of entities" means clusters that are different because entities within one cluster having at least one discretely measurable common property that is not shared with the entities within the other cluster(s). Thus clusters of entities can be distinguished from one and another by the measurement of any of the discretely measurable common properties shared by entities within one cluster but not by entities within the other cluster(s)—the distinct discretely measurable common properties.

For example, the clusters of entities can be distinguished by sizes, density or solidity including elasticity, brittle fracture, water-content etc. The particle size can be measured, for example, in a flow cytometry apparatus by so-called forward or small-angle scatter light or by microscopic examination. The clusters of entities can also be distinguished by shape. The shape of the particle can be discriminated, for example, by flow cytometry, by high-resolution slit-scanning method or by microscopic examination. The shape of a printed dot, for example, can be measured by a scanner. The clusters of entities can further be distinguished by tags, such as by fluorescent dyes with different emission wavelengths. Even when they are labeled with the same tag(s), the clusters of entities can still be distinguished because of different concentrations, intensity, or amounts of the tag associated with the entities, or the different ratios of tags on individual entities. Clusters of entities can be distinguished even when all entities share one or more discretely measurable common properties (e.g., particle size and particle shape), but do not share at least one other discretely measurable common property (e.g., intensity or amount of fluorescent tag per entity).

Methods known to a person skilled in the art can be used to measure the quality or quantity of tags. In addition, the clusters of entities can be differentiated by other property or characteristic of the entities, such as being magnetic or not. When the entities are composed of or labeled with nucleic acid or peptide molecules, the clusters of entities can be differentiated by their sequences.

As used herein, the term "entity" means a thing or composition that can exist separately or independently from other things. Examples of entities that can be used in the present disclosure include, but are not limited to, microparticles, nucleic acid molecules, or peptides/polypeptides.

As used herein, the terms "microparticle", "microsphere", "microbead", "bead", "microsphere", and "particle" are used interchangeably and bear equivalent meanings with respect to their particulate nature, understanding that particles can have various shapes and sizes. Preferred particles range in size from approximately 10 nm to about 200 μm in diameter or width and height in the case of nonspherical particles. For example, the particles can have a size of 0.05-50 μm, 0.1-20 μm, 1-20 μm, or 3-10 μm in diameter. The microparticles can have a different shape, such as a sphere, cube, rod or pyramid.

Those of ordinary skill in the art can use microspheres of various compositions. For example, styrene monomers polymerized into hard rigid latex spheres have been used as calibration aids at high magnifications. These latex spheres are known for their high level of inertness in the electron beam, and clusters constructed from groups of such particles within non-overlapping size ranges of approximately 0.05 to 2 microns may be detected by electron microscopy or light-scattering investigations. Likewise, the particles can be made of many other types of materials. For example, the microparticles can be made of polystyrene or latex material. Other types of acceptable polymeric microspheres include, but are not limited to, brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, POLYOX, EUDRAGIT, sugar spheres, hydrofuran, PLGA (poly(lactic coglycolic acid)) or combinations thereof. In general, such particles can be made by a copolymerization process wherein monomers, e.g., unsaturated aldehydes or acrylates, are allowed to polymerize in the presence of one or more tags, e.g., fluorescein isothiocynate (FITC), in the reaction mixture (see for example U.S. Pat. No. 4,267,234 issued to Rembaum; U.S. Pat. No. 4,267,235 to Rembaum et al; U.S. Pat. No. 4,552,812 to Margel et al.; and U.S. Pat. No. 4,677,138 to Margel). The microparticles can be produced, for example, by extrusion or spheronization. Rolland et al., J. AM. CHEM. SOC. 9 VOL. 127, NO. 28, 2005 describe the production of exemplary uniform, sub-micron, biodegradable particles produced in different shapes, such as a spheres, cubes, rods or pyramids, that can optionally encapsulate fluorescent material, among other things.

To increase the per volume information content, the entity can be labeled with one or more tags that are visible or invisible to naked eyes. The term "tag" or "taggant" as used herein can be any composition that is suitable for the purpose of detecting or identification. The tag can be overt, covert, or invisible or otherwise difficult to detect on individual entities or small numbers of entities, yet having an overt signal detectable from all or a larger number of entities. For example, the entity can be labeled with one or more colors, fluorescent dyes, ultraviolet radiation dyes, luminescent compositions, hapten, nucleotides, polypeptides, or scents. A single entity can be labeled with more than one tag of the same or different types. For example, a particle can be labeled with two or more discretely distinguishable dyes in varying proportion; or a particle can be labeled with a nucleotide and a fluorescent dye. Any of the known tags and the combinations of the tags with entities can be used in the present disclosure. Methods known to those skilled in the art can be used to label an entity with one or more tag. For example, U.S. Pat. No. 6,632,526 teaches methods of dyeing or staining microspheres with at least two fluorescent dyes in such a manner that intra-sample variation of dye concentrations are substantially minimized. The entity can be a segmented particle whose composition is varied along the diameter or the length of the particle. U.S. Pat. No. 6,919,009 teaches methods of manufacture of rod-shaped particles.

In one particular embodiment, the entity can be an entity that is labeled with or affixed to other entities. For example, the entity can be a symbol printed with an ink containing microparticles. Another example of an entity, according to this embodiment, is a particle that is covalently or non-covalently affixed with one or more other particles. U.S. Patent Application Publication No. 2006/0054506 describes submicron-sized particles or labels that can be covalently or non-covalently affixed to entities of interest for the purpose of quantification, location, identification, tracking, and diagnosis.

The entity that can be used in the present disclosure preferably can be ingestible and/or non-toxic in amounts used. For example, the entity can be a liposome microparticle, i.e., a particle formed by a lipid bilayer enclosing an aqueous compartment. The entity can also be a microparticle made of pulverized cellulose material, see for example the abstract of Japanese Patent Application No. JP0 6,298,650. The entity can further be microparticles made of calcium, such as milk calcium, inorganic calcium or organic calcium. For example, edible oil-containing calcium microparticles can be obtained following the teaching of U.S. Pat. No. 6,159,504. Biodegradable polymers, such as dextran and polylactic acid, can also be used to prepare ingestible microparticles. In addition, the edible microparticles include solid lipophilic microparticles comprising a lipophilic substance, hyaluronic acid or an inorganic salt thereof. Exemplary lipophilic particles are disclosed in U.S. Patent Application Publication No. 2003/0064105.

The entity can be magnetic. U.S. Pat. No. 6,773,812 describes hybrid microspheres constructed using fluorescent or luminescent microspheres and magnetic nanoparticles. Distinct clusters of microspheres can be constructed based on fluorescent intensities by analogy to the clusters described in Example 1 infra, and as provided in International Patent Application Publication No. WO 01/464774, and separations can be affected based on the variable degree of magnetic content to aid in the analysis of the cluster membership on devices like the Immunicon CELLSEARCH instrument. The various microspheres disclosed in U.S. Pat. No. 6,773,812 can be used in the present disclosure. The particles can also have any other property that facilitates collection, separation, or identification of the particles.

The entity can also be made of chemically inert materials to enhance the survival of the entity in a chemical or biological environment, including materials resistant to heat, high or low pH, etc. The entity can further be made of materials that are non-toxic, or materials that can serve as carriers for the active ingredient. The entity can even be made from the active ingredient of a pharmaceutical product.

As used herein, a "population of entities" or a "population" means a collection of a combination or plurality of entities that include two or more distinct clusters of entities, wherein entities within one cluster have one or more discretely measurable common properties that are different from that of entities within another cluster from the same population.

As used herein, the term "relative counts of entities per cluster" means a ratio of the count of entities per cluster relative to another number. In some embodiments, the other number is the count of entities within a different cluster. In other embodiments, the other number is the total count of entities within two or more clusters of a population of entities. In other embodiments, the other number is representative of the amount or concentration of the cluster or the population of entities, such as unit volume or weight of the cluster or the population of entities. In yet other embodiments, the other number is representative of the amount or concentration of a product the cluster is associated with, or the amount or concentration of a portion or a component of the product.

As used herein, the term "a representative number of entities within a population of entities" refers to a fraction or a portion of the population of entities which contains the same clusters of entities and the same count of entities per unit of each cluster as those of the population.

For illustrative purpose, in one specific embodiment of the present disclosure, the population of entities is composed of microparticles each simultaneously labeled with two or more fluorescent dyes, for example, according to U.S. Pat. No. 6,632,526 or U.S. Pat. No. 6,649,414. The microparticles can also be purchased from a commercial source, such as Luminex Corporation (Austin, Tex.). For example, the particles can be labeled with two dyes, such as a red fluorescent dye, 1,3-bis[(1,3-dihydro-1,3,3-trimethyl-2H-indol-2-ylidene)methyl]-2,4-dihydroxy-cyclobutenediylium, bis(inner salt) (Dye 1) and an orange fluorescent dye, 2-(3,5-dimethylpyrrol-2-yl)-4-(3,5-dimethyl-2H-pyrrol-2-ylidene)-3-hydroxy-2-cyclobuten-1-one (Dye 2). As is readily appreciated, other combinations of dyes with other colors and other chemical compositions can also be used to label microparticles. One skilled in the art can select among a variety of suitable dyes such as, for example, the dyes recited in U.S. Pat. No. 6,649,414, depending upon desired emission/absorption and hydrophobic properties, etc. Where fluorescent dyes are used, the dyes are chosen such that the emission maxima of the dyes used preferably falls about in the center of the fluorescence detection channels of the measurement device used. Preferably the dyes used have emission maxima separated by greater than 10 nm, 25 nm, or 50 nm from each other.

Microparticles within the population are heterogeneous because they do not share at least one distinctly measurable property (e.g., intensity or amount of fluorescent tag per entity). The fluorescent intensity of the red or orange dye on each microparticle can be measured by flow cytometry.

As used herein, "a signature array of a population of entities" is an array comprising information about the counts or relative counts of entities of at least two distinct clusters of entities within the population. For example, a signature array comprises information about the counts of microparticles within each distinct cluster of the population. Each cluster is different from one another by at least one distinct discretely measurable common property.

The method of product authentication of the present disclosure uses a product authentication code defined by the nucleotide sequence of a target nucleic acid and/or signature array of a population of entities, which has high per volume information content.

As used herein, a "product authentication code" or "product identification code" is a system that represents information specific to a product. The system or code is matched with a particular product or batch of products such that tacking or sampling of the code associated with the particular product or batch of products provides those individuals designated by the source originator of the code or the commercial user of the code to know any of a variety of characteristics or information about the product(s). For example, a "product authentication code" for a pharmaceutical product can represent information about the product, such as the chemical composition, the concentrations of the effective ingredients, the date or place of manufacture, the source of distribution, the batch, the shelf life, or a myriad of other information designations.

For the purposes of the present disclosure, the term "substrate" represents any particulate or non-particulate material to which or upon which an oligonucleotide can be immobilized.

In certain embodiments, nucleic-acid based product authentication method of the present disclosure for detecting a target nucleic acid rely on a set of measurements of a first parameter or parameters in order to identify an entity within a population of entities comprising a signature array. A corresponding set of measurements of a second parameter or parameters is made to determine the presence of, or to quantify a target nucleic acid. The entity identification and target determination parameters are used to generate a correlated data list. These parameter measurements can be made sequentially. Each set of measurements is referred to as an event. Thus, a data list can appear as follows:

| Event | Parameter X | Parameter Y | parameter Z |
|---|---|---|---|
| 1 | X1 | Y1 | Z1 |
| 2 | X2 | Y2 | Z2 |
| 3 | X3 | Y3 | Z3 |
| ... | ... | ... | ... |
| N | Xn | Yn | Zn |

Such data lists are typically obtained using laser scanning cytometry or flow microfluorimetry. They are generally referred to as "list-mode data."

A range of values for a single parameter X ("A") can be used to define a cluster of entities that bear a first target nucleic acid. Another range of values for X ("B") can be used to define for a cluster of entities that bear a second target nucleic acid. By this means, both assays for both the first and second target nucleic acid can be carried out simultaneously. Whenever an event is correlated with a value for X, in range A, the measurement of parameter Z would be for the first target nucleic acid. Whenever an event is correlated with a value for X, in range B, the measurement of parameter Z would be for the second target nucleic acid. The number of assays for different target nucleic acid that can be carried out simultaneously is limited only by the number of discrete ranges that can be detected within the parameter X being used to specify an entity for each target nucleic acid. A high degree of certainty can be obtained that events belong to a particular entity class (i.e., cluster) by setting broad ranges for A, B, etc.

The number of assays that can be carried out simultaneously can be increased if more than one parameter is used to define a cluster of entities that bear a target nucleic acid. A range of values for parameter X ("A") in conjunction with a range of values for parameter Y ("Q") can be used to define a cluster of entities that bear for a first target nucleic acid. Another range of values for X ("B") in conjunction with another range of values for parameter Y ("R") can be used to define a cluster of entities that bear for a second target nucleic acid.

By this means, assays for both the first and second target nucleic acid can be carried out simultaneously. Whenever an event is correlated with a value for X, in range A, and Y, in range Q, the measurement of parameter Z would be for the first target nucleic acid. Similarly, whenever an event is correlated with a value for X, in range B, and Y, in range R, the measurement of parameter Z would be for the second target nucleic acid. When using multiple parameters to identify each cluster of entities that bear a target nucleic acid, the number of assays for different target nucleic acid/cluster combinations that can be carried out simultaneously is no longer limited by the number of discrete ranges of an individual parameter, since a specific combination of parameters can be used to specify an assay for each target nucleic acid. Additionally, a higher degree of certainty can be obtained that events belong to a particular assay class by setting broad ranges for A, B, Q, R, and so on.

In laser scanning cytometry or flow cytometry, the preferred parameters for classifying multiple simultaneous assays are forward light scatter, side scatter, or a fluorescence parameter(s) distinct from that used to detect signal from hybridized nucleic acids. For DNA chips, the preferred parameters for classifying multiple assays are spatial dimensions, x and y coordinates or positions on the surface of the chip.

A major advantage of the present disclosure, in addition to allowing multiple assays to be carried out simultaneously, is the ability to obtain replicate measurements of the same assay using the list mode data. For example, events 1 through n are classified as belonging to an assay for a first target nucleic acid, based upon measurements within a range of values for parameter X ("A") in conjunction with measurements within a range of values for parameter Y ("Q"). Events n+1 through p are classified as belonging to an assay for a second target nucleic acid, based upon measurements within a range of values for X ("B") in conjunction with measurements within a range of values for parameter Y ("R").

Statistical analysis can be performed to determine the mean and standard deviation of Z for the first assay by analyzing events 1 through n. Similarly statistical analysis can be performed to determine the mean and standard deviation of Z for the second assay by analyzing events n+1 through p. Thus, differences in signal between a target and control and between target levels can be expressed as differences between means of replicate measurements, thereby, enhancing the sensitivity of all assays performed. Events belonging to a particular assay class do not have to be measured sequentially. They have been shown as occurring sequentially for illustrative purposes only.

Another advantage is that a single parameter can be used to detect the signal from multiple target nucleic acids simultaneously. Thus, only one reporter element is necessary, regardless of the number of target nucleic acids to be determined. Conjugates of fluorescein isothiocyanate (FITC) are useful for signal generation. In preferred embodiments, an intercalating dye is used.

The determination of the presence or amount of double-strand or duplex nucleic acid in the presence of single-strand nucleic acid can be accomplished using a compound which upon binding or when bound to duplex nucleic acid, produces a detectable change in an optical property such as absorption or fluorescence (Ririe et al., *Anal Biochem* 245, 154 (1997), Wittwer et al., *BioTechniques* 22, 130 (1997), Yamamoto et al., European Patent Publication 0 643 140 A1 and U.S. Pat. Nos. 5,049,490 and 5,563,037 to Sutherland et al.).

Nucleic acids can be determined using a "nuclease protection assay" as described in Sambrook et al. in *Molecular Cloning: A Laboratory Manual*, Vols. 1-3, 2nd ed., Cold Spring Harbor Laboratory Press, Cold Spring Harbor, N.Y. (1989) and Thompson et al., *Biol. Chem.* 267, 5921 (1991). This method involves hybridization of a labeled, single-strand DNA probe to a target DNA or RNA molecule and subsequent hydrolysis of single-strand nucleic acid by a single-strand specific endonuclease, such as S1 nuclease. Hybridized duplex nucleic acid remains intact, protecting the labeled probe from hydrolysis by the endonuclease. The label can be a dye, a fluor, a radiolabeled molecule, an enzyme, and so on as recognized in the art, and appropriately detected. The assay can be quantitative for the target nucleic acid.

Nucleic acid amplification methods, such as the Polymerase Chain Reaction (PCR), often provide for the detection of a target nucleic acid using a labeled probe or, alternatively, a labeled primer that is extended into detectable product captured onto an immobilized complementary oligonucleotide probe. A wide variety of labels have been developed, Vlieger et al., *Anal Biochem* 205, 1 (1992), Yang et al., *Blood* 81, 1083 (1993). Fluoresceinated primers have been used in flow cytometric detection of bcl-2/MBR and IgH gene rearrangements, Barker et al., *Blood* 83, 1079 (1994).

Another method for determining a target nucleic acid involves linear amplification of signal from a target-specific oligonucleotide probe labeled with a fluorophor. The labeled probe, when hybridized to target, is hydrolyzed by a duplex nucleic acid-specific exonuclease, such as exonuclease III, which hydrolyzes duplex DNA (dsDNA) from the 3' terminus. Truncated hetero-duplex hybrids produced during hydrolysis are unstable. Shortened fragments of labeled probe dissociate. Fresh, intact, labeled probe can then hybridize to the target and a new round of hydrolysis occurs followed by dissociation of shortened, labeled probe and so on. The resulting probe fragments are then separated by electrophoresis and determined using a sequencing apparatus. (Okano et al. *Anal Biochem* 228, 101 (1995)).

Tyagi et al., *Nature Biotechnolgy* 14, 303 (1996), have described the use of, so-called, molecular beacons for the detection of nucleic acids. A molecular beacon is a target-specific oligonucleotide comprising a fluor, and in close proximity to the fluor, a quencher. Upon binding of target nucleic acid, the fluorophore and quencher become separated, and the resulting fluorescence is detected.

In the case of a plurality of distinct target nucleic acids, a target-specific substrate/particle is rendered specific to a distinct target nucleic acid by having immobilized thereto an oligonucleotide complementary to at least a portion of only one distinct target nucleic acid. Target DNA can be in single-strand (ssDNA) or duplex form. If in duplex form, it can be treated, usually by heating to denature the dsDNA prior to, during, or subsequent to combination with a substrate-immobilized oligonucleotide. The ssDNA target is then allowed to hybridize to substrate-immobilized oligonucleotide.

Any optical signal and method of producing it that is derivable from or associated with target nucleic acid hybridized to substrate-immobilized oligonucleotide can be used in the practice of this present disclosure. As noted, in one embodiment, target-correlated signal is obtained by utilizing a dyefluorophore that binds to dsDNA and produces a detectable fluorescence signal when so bound. This is illustrated schematically in FIG. 1. Alternatively, a fluorescence signal associated with target hybridized to substrate-immobilized oligonucleotide can be produced by utilizing a fluorophore linked to the oligonucleotide. When the substrate-immobilized oligonucleotide probe is hybridized to target nucleic acid to form duplex nucleic acid, single-strand specific endonuclease is not able to hydrolyze or substantially hydrolyze the oligonucleotide, or therefore, the portion of oligonucleotide having the fluorophore linked thereto. Thus, fluorophore linked to oligonucleotide remains associated with the substrate; target-correlated signal originating from the fluorophore that is associated with hybridized target is detected. Signal originating from fluorophore that is released by single-strand endonuclease mediated hydrolysis does not substantially contribute to the measured fluorescence.

In a related embodiment, restriction endonuclease mediated hydrolysis can be used to release a fluorophore bound to the oligonucleotide, upon creation of a double strand DNA sequence that contains a restriction site when target hybridizes to substrate-immobilized oligonucleotide. In another embodiment, a fluorophore is bound to the oligonucleotide or the substrate so as to be sufficiently close to a compound capable of substantially quenching (by greater than or equal to about 50%) its fluorescence. If the fluorophore is linked to the substrate then the quencher is linked to the oligonucleotide. If the quencher is linked to the substrate then the fluorophore is linked to the oligonucleotide. Or fluorophore and quencher can both be linked to the oligonucleotide.

The ability of a dye to produce a detectable signal only when bound to dsDNA, although preferred, is not a requirement of a dye in order for it to be useful in practicing the presently disclosed subject matter.

Particles and Particle-Immobilized Oligonucleotide

Particle substrates of the present disclosure may be composed of any material or combination of materials that will enable covalent or non-covalent linking of oligonucleotide and/or other compounds such as fluorophores. They can be of a construction that allows compounds such as fluorophores to be encapsulated, as long as the fluorescence is detectable. They can be of a size and composition so as to scatter electromagnetic radiation. Preferably, the particles are composed of one or more polymers comprising ligands or functional groups that enable non-covalent or covalent bonding of oligonucleotides and/or other compounds directly or through suitable binding partners or linker groups. Preferably, they are substantially spherical and have a diameter in a range from about 0.3 microns to about 50 microns, more preferably 0.9 microns to about 15 microns and/or are capable of scattering electromagnetic radiation greater than or equal to about 200 nanometers. Polymeric particles for use in the practice of the present disclosure can be prepared by methods known to the skilled artisan. See, for example, U.S. Pat. Nos. 4,997,772, 5,149,737, 5,210,289 and 5,278,267 and references cited therein. Alternatively, suitable particles can be obtained for instance, from Bangs Labs, Fishers, Ind. and Spherotech, Libertyville, Ill. and others known to the skilled artisan. The particles may be attached in or on to the articles to be authenticated through various means known in the art. Particle retention can be achieved using appropriate materials, for example, a mesh incorporated into the product or binding agents such as starches or sprays having adhesive properties.

The attachment of oligonucleotides to particulate and non-particulate substrates can be carried out using methods that are well known, as described, for example, in U.S. Pat. Nos. 5,177,023, 4,713,326, 5,147,777, 5,149,737, European Patent Application No. EP-B-0 070 687, International Patent Application Publication No. WO-A-88/01302, and references cited therein. An oligonucleotide can have linked to it any desired compound or compounds as long as the compound or compounds do not substantially interfere with hybridization of the target nucleic acid. For example, a ligand such as biotin, a fluor, a fluorescence quenching compound, or other compound(s) can be so linked. An oligonucleotide can be linked to a particle at its 3' or 5' end.

An oligonucleotide probe can comprise any desired number of bases. In general, it can comprise a base length between about 5 to about $10^5$ nucleotide bases. Preferably, it comprises a base length between about 15 to about 40,000 bases, more preferably between about 30 to about 10,000 bases, and even more preferably between about 30 to about 1000 bases, and most preferably between about 30 to about 500 bases.

Target Nucleic Acid Spotting

One method of immobilizing target nucleic acid unto products to be authenticated is to use the "sticky" polymer method of Sheu, Jue-Jei; et al., U.S. Patent Application Publication No. 2005/0008762, the disclosure of which is incorporated herein by reference. In the Sheu, Jue-Jei method, a water-insoluble medium comprising polymeric substances is first dissolved in an organic solvent to form a medium/solvent mixture. Then, target nucleic acid solution in water, TE buffer or other suitable buffer, is mixed with an intermediate solution, such as methanol, ethanol, acetone, glycerol or their mixtures to form a homogenous mixture of nucleic acid solution. The two mixtures are mixed to form a third homogenous mixture which is then spotted or spread on the product to be authenticated. After drying, the nucleic acid taggants protected by the water-insoluble medium adhere on the surface of the object. A liquid object may be similarly marked.

The water-insoluble medium comprises polymeric substances such as polypropylene (PP), polymethyl methacrylate (PMMA), polycarbonate (PC) and polystyrene (PS). The organic solvent could be any one of chloroform, dichloromethane and benzole solvent, such as xylene or toluene or other organic solvent known in the art.

The gene pen apparatus of Friedman et al., U.S. Pat. No. 6,235,473, may be adapted for printing target oligonucleotides unto products to be authenticated. Friedman et al.'s apparatus, the entire disclosure of which is incorporated herein by reference, comprises a reservoir containing an oligonucleotide, the reservoir being fluidly connected to a printing head, the printing head comprising a flow controlling means, especially a pin valve means or a felt tip means for printing target nucleic acids on a product.

Detection

An important aspect of the present disclosure with particulate substrates is the use of methods and instrumentation capable of distinguishing particles and target-correlated signal over background, and target-specific particles, one from another, based on the light scattering and/or fluorescence properties of the particles. Target-specific particles are distinguishable, one from another, by the distinct differences in their light scattering properties and/or the distinct differences in the fluorescence signals derived from a fluorophore or plurality of fluorophores associated with each target-specific particle, which fluorescence signals are distinct from target-correlated fluorescence.

Light scattering by a particle depends on its size and/or refractive index, both of which can be modified as desired using well known methods. It is not necessary for a particle to be capable of scattering light. Particle discrimination can be achieved by incorporating, encapsulating, non-covalently or covalently bonding to a particle one or more compounds that are capable of producing distinct fluorescence.

Laser scanning cytometry has been used for distinguishing particles, such as blood cells. When a cell or group of cells (agglutinate) is scanned by the laser light beam, the illuminating light is scattered by the cell or group of cells; the intensity of scatter being a function of cell (or agglutinate) size and shape. For example, individual red blood cells scatter less light than small agglutinates, which in turn scatter less light than large agglutinates.

Similarly, when a cell or group of cells (agglutinate) is scanned by the laser light beam, the illuminating light can induce fluorescence from a fluor(s) associated with a cell or cells. If a fluorophore is relatively uniformly associated with a cell, the fluorescence intensity is related to agglutinate size. For example, individual red blood cells would fluoresce less than small agglutinates which in turn, would fluoresce less than large agglutinates.

Using scattered light and fluorescence in combination is more reliable than using either alone for discriminating different classes of agglutinates.

In flow cytometry, particles, such as blood cells, are introduced into the center of a fast moving fluid stream and forced to flow single file out a small diameter orifice at uniform speeds. The particles are hydrodynamically focused to the center of the stream by a surrounding layer of sheath fluid. The particles within the stream pass a measurement station where they are illuminated by a light source and measurements, in the case of red blood cells, are made at rates of $2.5 \times 10^2$ to $10^6$ cells per minute. Laser light sources are used in the measurement of particles; typical laser light sources used include argon ion lasers (UV, blue and green light), krypton lasers (yellow and red light), helium-cadmium lasers (UV and blue light), and helium-neon lasers (red light).

In fluorescence microscopy, particles can be detected on a microscope slide or equivalent. Typically, they are illuminated by a white light source or a substantially monochromatic light source. Here too, laser light sources may be used as the source of the monochromatic light. The presence of particles may be assessed with the white light, and the associated fluorescence assessed with monochromatic light and appropriate filters. Visual or automated means may be used for one or both of these readings.

A preferred flow cytometer is capable of selecting for the detection of target-correlated signal associated with particles having a defined range of forward-angle and right-angle scattering signal intensity or particular fluorescence (Yang, et al. *Blood* 81, 1083 (1993), Barker et al. *Blood* 83, 1079-1085 (1994), Chandler, et al., *ISAC XIX International Congress*, Colorado Springs, Colo. USA, Fulton, et al., *Clinical Chem* 43, 1749 (1997), Fulwyler, et al., *Methods Cell Biology*, Second Edition, Academic Press, v 33, 613 (1990), and McHugh, *Methods Cell Biology*, Second Edition, Academic Press, v 42, 575, (1994)). Data acquisition is initiated by light scattering and/or fluorescence associated with a particle. Selecting for signal associated with a particle enables the detection of target-correlated signal without interference from fluorescence originating from the bulk solution phase in which the particles are immersed. Thus, the signal/noise ratio is large. Target-correlated signal is proportional to the amount of target, and determination of multiple target nucleic acids is also possible using the preferred flow cytometric methods. Multiplex analysis of nucleic acids that are free in solution using flow cytometry has been described by Chandler et al., *ISAC XIX International Congress*; Colorado Springs, Colo. (1998), Fulton et al., *Clin Chem* 43 1749(1997), Fulwyler et al., *Methods Cell Biology*, $2^{nd}$ Ed. 613(1990), and McHugh, *Methods Cell Biology*, $2^{nd}$ Ed. 575(1990).

DNA Binding Fluorophores

Numerous compounds capable of binding to dsDNA and producing a detectable signal when bound thereto or which can be chemically modified to produce a detectable signal are known and available to the skilled artisan. Included among them are dyes, antibiotics, and chemotherapeutic agents. They can be intercalating or non-intercalating; but, they must not bind substantially to the substrate to which oligonucleotide is immobilized. Specific examples include, but are not limited to, acridine orange, propidium iodide, ethidium bromide, mithramycin, chromomycin, olivomycin, see also, U.S. Pat. Nos. 5,049,490 and 5,563,037. Preferred compounds include Hoechst H33258, Hoechst H33342, DAPI (4',6-diamidino-2-phenylindole), and from Molecular Probes, TOPRO, TOTO, YOPRO, YOYO, SYBR GREEN I, Picogreen dsDNA Quantitation Reagent, and Thiazole Orange. Some compounds, such as YOYO, are virtually non-fluorescent until they bind dsDNA. Acridine orange has metachromatic properties that allow distinction between binding to ssDNA or dsDNA. For the purposes of the present disclosure, a compound either must not substantially bind to single strand immobilized oligonucleotide, but if it does, any resulting signal must be capable of being differentiated from that produced when the compound is bound to dsDNA.

Single-Strand Specific Endonucleases, Restriction Endonucleases

Single-strand specific endonucleases that can be used in the practice of this presently disclosed subject matter include, but are not limited to, S1 endonuclease and mung bean endonuclease. Restriction endonucleases that can be used include, but are not limited to: Acc65 I, Acc I, Aci I, Alu I, Apa I, ApaL, Ava I, Ava II, Bae I, BamH I, Bcg I, Bcl I, Bfa I, Bgl I, Bgl II, Bsa I, BsaJ I, Bsl I, BspH I, BsrG I, Bst4C I, BssS I, BstE II, BstU I, BstX I, BstY I, Cla I, Dde I, Dpn I, Dpn II, Dra I, Dra III, Eco0109 I, EcoR I, EcoR V, Fau I, Fok I, Hae II, Hae III, Hha I, Hinc II, Hind III, Hinf I, Hpa I, Hpa II, Kpn I, Mbo I, Mlu I, Mnl I, Mse I, Msp I, Nae I, Nco I, Nde I, Nhe I, Nla III, Nru I, Pst I, Pvu I, Pvu II, Rsa I, Sac I, Sac II, Sal I, Sau3A I, Sca I, Sfi I, Sma I, SnaB I, Spe I, Sph I, Ssp I, Stu I, Sty I, Taq I, Xba I, Xcm I, Xho I, Xma I, and Xmn I.

Fluorophore and Quencher

In an embodiment wherein a fluorophore and a quencher are provided together, a fluorophore can be linked at or near a terminus of an oligonucleotide and a quencher can be linked at or near the other terminus, as in a stem-loop structure (molecular beacon) described by Tyagi et al., *Nature Biotechnolgy* 14, 303 (1996), Tyagi et al., *Nature Biotechnolgy* 16, 49 (1998), Giesendorf et al., *Clin Chem* 44, 482 (1998), and Estrada et al., *Mol Cell Probes* 12, 219 (1998). In a stem-loop structure the oligonucleotide comprises complementary nucleotide base pairs at both termini. Hybridization of the complementary base pairs results in formation of a closed loop with the fluorophore and quencher in sufficient proximity so that fluorescence is quenched. Upon hybridization of target nucleic acid to the oligonucleotide, the loop is opened and fluorophore and quencher become sufficiently separated to allow fluorescence.

In all cases, separation of substrate-immobilized oligonucleotide from the matrix in which it is immersed is not required prior to detection. However, such separation may be carried out, if desired, using well-known methods such as filtration, centrifugation or magnetic separation.

While this disclosure describes detection of PCR products by mixing these with microspheres and intercalating dyes, further disclosed is the addition of the microspheres-immobilized oligonucleotide probes and the intercalating dyes to the PCR reaction before, as an alternative to after, thermocycling. In this embodiment of the present disclosure, either the dye (in this embodiment, preferably a thermostable dye) or the microspheres, alone, could be in the mix prior to thermocycling, or alternatively, both may be present. Accordingly, the amount of target oligonucleotide used and sample handling can be even further reduced when measuring PCR products either in the homogeneous formats described herein above and in Example 6 hereof, or in other formats that might be used or developed by one skilled in the art.

Materials and Methods for Examples

Unless indicated otherwise, the particles used in the examples were copolymers of (poly[styrene-co(p-vinylbenzylthio)proprionic acid] 97.6:2.4 molar ratio) prepared as described in U.S. Pat. Nos. 5,149,737; 5,210,289 and 5,278,267. The particles were substantially spherical and approximately 1.7 micrometers in diameter. Coupling of oligonucleotide to the particles was carried out essentially as described in U.S. Pat. No. 5,147,777. Unless indicated otherwise, oligonucleotides were synthesized using procedures well known in the art. Two oligonucleotides used in the examples are identified below:

```
SEQ ID NO: 1:
5'-TTTCCAAGTA AGCAATAACG TCAGCTCTTT CTTGTGGCTT

CTTCATACCA GCGAAAGACA TCTTAGTACC TGGCATGAAC

TTCTTTGGGT-3'.
```

The above oligonucleotide was modified by linking biotin to the 5' terminus through two tetraethylene glycol (TEG-TEG) spacers with and without an aminodiol (ADL) linker at the 3' terminus for attachment to a particle as represented by the following:

```
Oligo-1A:
Biotin-TEG-TEG-5'-TTTCCAAGTA AGCAATAACG

TCAGCTCTTT CTTGTGGCTT CTTCATACCAG CGAAAGACAT

CTTAGTACCT GGCATGAACT TCTTTGGGT (SEQ ID NO: 1)-
3'-TEG-TEG-ADL-Particle.
and
```

```
Oligo-1B:
Biotin-TEG-TEG-5'-TTTCCAAGTA AGCAATAACG TCAGCTCTTT

CTTGTGGCTT CTTCATACCAG CGAAAGACAT CTTAGTACCT

GGCATGAACT TCTTTGGGT (SEQ ID NO: 1)-3'.

SEQ ID NO: 2:
5'-ACCCAAAGAA GTTCATGCCA GGTACTAAGA TGTCTTTCGC

TGGTATGAAG AAGCCACAAG AAAGAGCTGA CGTTATTGCT

TTGGAAA-3'.
```

Sequence Generation

DNA sequences were designed for safe use as tracer ingredients in biological environments. Some examples of biological environments include biological specimens, products intended for injection like injectable pharmaceuticals, and substances that may enter a living ecosystem.

The first method of DNA sequence design involved the selection of sequences that have few or no occurrences in naturally occurring DNA. Because DNA encodes information that is used by living organisms for creating biological molecules, a DNA tracer sequence that has minimized similarity to the sequences found in nature is expected to be biologically inert by comparison, and therefore more safe than naturally occurring sequences.

The second method of DNA sequence design incorporated the additional requirement that one or more stop codons be incorporated with the DNA sequence. Stop codons terminate protein translation from DNA sequence, so their presence is expected to enhance biological inertness and therefore their safety. For demonstrative purposes, the sequences identified below include stop codons in a number of different locations relative to the sequence.

Sequence Set #1: DNA Sequences Designed for Minimal Similarity to Naturally Occurring DNA Sequences Using software written in the R language, a random number server (random.org) was used to generate random integers based on atmospheric noise. These numbers, integers between 1 and 4, were then translated to nucleic acid bases ("A," "T," "G," "C") and concatenated into sequences of a user-specified length (in this case, 35 nucleotides long). To ensure that sequences were unique and not present in nature, the sequences were batch-screened against the National Institute of Health BLAST database of known biological sequences, retaining four of those sequences with the fewest alignments. Those sequences were:

```
SEQ ID NO: 7:
5'-TTA AAT AGG TAT CGC GTG CTT ACT CCG GTG GAC

CG-3'.

SEQ ID NO: 8:
5'-TCG CAC TTA TCT CGT ACC GTG AAC ACC TAG CGC

GT-3'.

SEQ ID NO: 9:
5'-GAT CGA CGT ACA TGC CCG ATC CAC GGA CAT TCT

TT-3'.

SEQ ID NO: 10:
5'-ACG ATC ACG CGT GCA ATT GGT ACA CGA GCC GAG

TC-3'.
```

Figure 7:
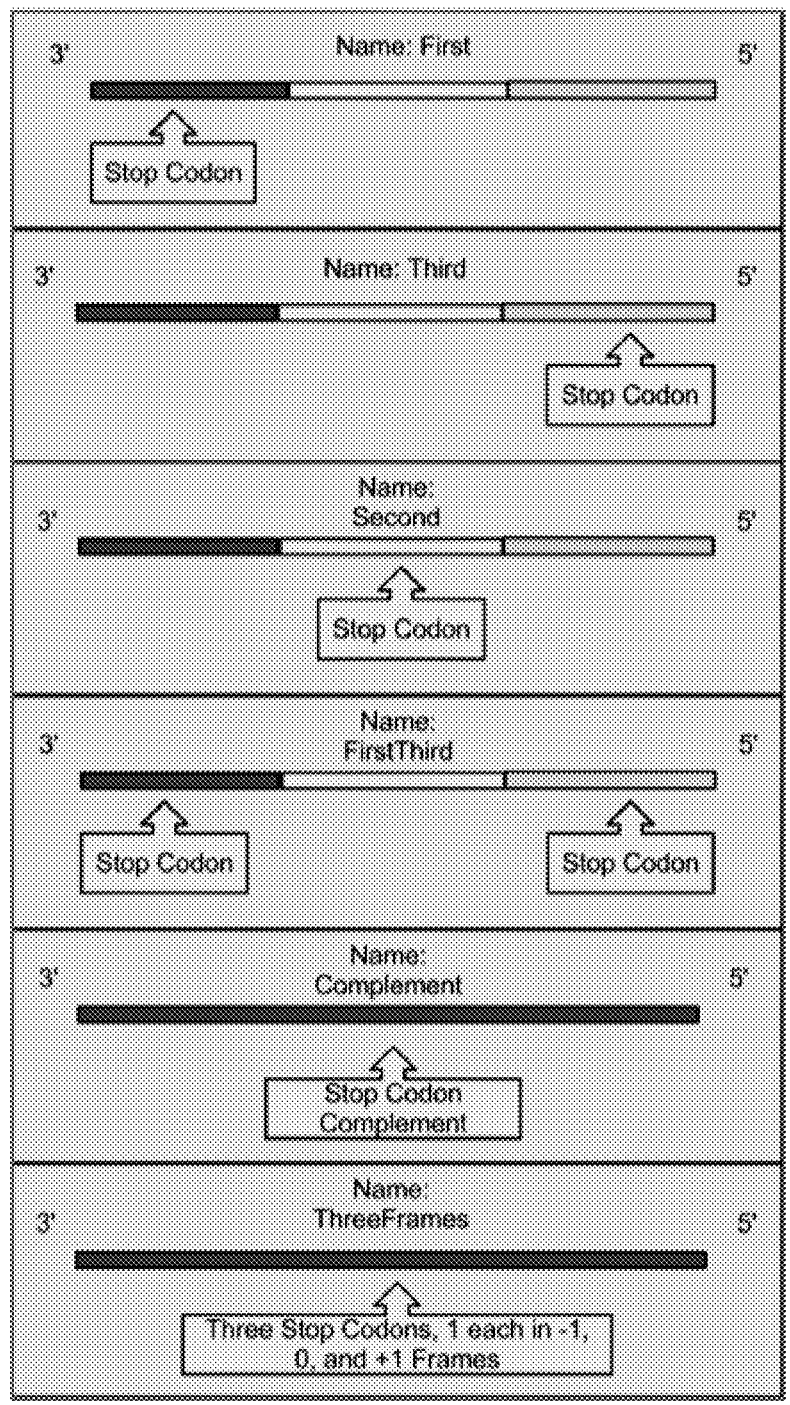
FIG. 7 shows a schematic of stop codon placement configuration options.

Sequence Set #2: DNA Sequences Designed for Both Minimal Similarity to Naturally Occurring DNA Sequences and Having Stop Codons Dispersed Throughout Using the R language, software was developed to generate random DNA sequence of user-specified length (in this case, 51 nucleotides long). One of three random DNA stop codons ("TAG," "TAA," or "TGA") was then intentionally inserted into the sequences at specified points. The software was designed to insert stop codons using one of six ways (see FIG. 7), and a name was given to each of the categories:

First: A stop codon is inserted within the first third of the sequence at a random point.

Third: A stop codon is inserted within the latter third of the sequence at a random point.

Second: A stop codon is inserted within the middle third of the sequence at a random point.

FirstThird: A stop codon is inserted within the first and latter thirds of the sequence at random points.

Complement: A stop codon complement ("ATC," "ATT," or "ACT") is inserted within the first and latter thirds of the sequence at random points.

ThreeFrames: A random stop codon is inserted in each of the three reading frames (−1, 0, and +1).

Figure 8:
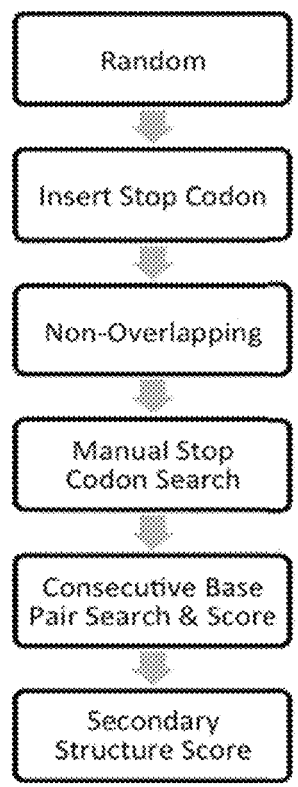
FIG. 8 is a flow chart containing the stepwise procedure for selecting nucleotide sequences that have minimized overlap with naturally occurring sequences and stop codons placed in one or more locations in the sequence.

Sequences meeting both the non-similarity requirement and one of the stop codon requirements were screened for additional desirable properties, described in the following section and summarized by the flow chart shown in FIG. 8.

Sequence Screening

Step 1: 120 random sequences were generated over three runs using R software code. The sequences were then passed through four filters: NIH's BLAST alignment algorithm tool, a manual check for inserted and additional background stop codons, consecutive mononucleotides (base repeats), and a general analysis of secondary structure.

Step 2: All random sequences generated by the R were then modified to include a stop codon in one of the six stop codon location configurations.

Step 3: Sequences from Step 2 were input into the National Institute of Health's Basic Local Alignment Search Tool (BLAST). Only those sequences having one or fewer alignments with known biological sequences were passed to Step 4.

Step 4: For those sequences with only one alignment, the length of that alignment in terms of nucleotide base counts was determined. Next, we performed a manual search for target codons for each stop codon location category, and the number of total codons is counted. This count was recorded for later reference.

Step 5: Sequences containing long nucleotide runs were screened. The number of runs for each of A, T, C, and G base pairs was counted. The longest run lengths were recorded for each base pair; the sum of run lengths for a single candidate sequence was used to create a preliminary unweighted score. Candidate sequences with lower scores were deemed to have a higher suitability for our purposes. Qualifying sequences were then passed to the next filter.

Step 6: The candidate sequences were analyzed for secondary structure at standard conditions (37° C., 1M Na+). Sequences exhibiting fewer secondary structures (loops, pseudo knots) were considered more favorable, and the number of these structures was noted for each sequence. A final score was calculated for each candidate sequence by summing the total base pair score and secondary structures score. Representative sequences from each category having the lowest scores were chosen as approved sequences. Exemplary sequences identified using this process are noted below, with stop codons underlined.

SEQ ID NO: 11:
5'-ACTAGATACCCAGCACGCCTTGGACGCGACATATCTCACCCCTGGA GCGGC-3'.

SEQ ID NO: 12:
5'-GAGCTCACAGTTCCTAAAGTGTAATGGCCGGCTACGCTAAGCGCAT TGATT-3'.

SEQ ID NO: 13:
5'-CAACGTGAGCTCTTATCACTCCTATCTGATTCCCTATCGATACATG CCAGG-3'.

SEQ ID NO: 14:
5'-GTCATAAGTATACTCCTCACACGGAGTCGCCACACCTATGAAGAGT AGTGT-3'.

SEQ ID NO: 15:
5'-GGTAGCACTAGTTGCTCCGAGAGGGTCTATTGCGGCCGCAGCCGGC CATAT-3'.

SEQ ID NO: 16:
5'-GTTGTCGTTGCGCCTGAATCTCGTATAAGATATACAGGGTGATCGA CGGCT-3'.

Hybridization Conditions

Hybridization of biotinylated oligonucleotide probe, (SEQ ID NO: 1) to target DNA (SEQ ID NO: 2) was carried out by incubating 100 fmoles of probe in 10 μL of 0.15M potassium chloride, 0.01M tris(hydroxymethyl)aminomethane (Tris), 1 mM ethylenediaminetetraacetic acid (EDTA), pH 8.3 in the presence of 1 μg of calf thymus DNA. DNA was denatured by heating for 3 minutes at 96° C., and the mixture was then incubated at 65° C. for 10 minutes to allow hybridization of target and oligonucleotide probe. Binding of the biotinylated oligonucleotide to streptavidin-coated beads (Bangs Laboratories) was carried out by supplementing the reaction mixture with $5 \times 10^4$ beads in a final volume of 15 μL and incubated the mixture for 10 minutes at room temperature.

Binding of Fluorophore

To a 500 μL aliquot of a working stock solution of fluorophore was added 10 μL of hybridized target-probe bead suspension and the mixture was incubated at room temperature for a minimum of 5 minutes. The working stock solution of fluorophore was prepared from the original preparation supplied by the manufacturer as follows: picogreen was diluted 1:10,000 with TE buffer, SYBR GREEN was diluted 1:200 with TE buffer, thiazole orange (Aldrich Chemical Company, Milwaukee, Wis.) 1 μg/mL in TE buffer, TOPRO-1, TOTO-1, YOPRO-1 and YOYO-1, all 0.5 μM in TE buffer.

Nuclease Protection

After hybridization of bead-immobilized oligonucleotide probes (SEQ ID NO: 1) to target DNA (SEQ ID NO: 2), an 8 μL aliquot of the suspension was combined with 8 μL of 2×S1 nuclease buffer or 2× mung bean nuclease buffer (Promega, Madison, Wis.), digested with 1 unit of S1 nuclease or mung bean nuclease, and incubated at 30° C. for 30 minutes. To the reaction mixture was added, a 1:10 dilution of streptavidin-conjugated phycoerythrin fluorophore in TE buffer to a final volume of 24 μL.

Flow Cytometry

Flow cytometric analysis was performed using an Ortho CYTORONABSOLUTE® Flow Cytometer with Immunocount 2.2 software. Parameters for particle analysis were determined for each lot of bead-immobilized oligonucleotide. Gains and amplifiers for forward-angle scattering and right-angle scattering were setup such that beads of each size could be detected and resolved by the instrument. Fluorescence gain and amplifier settings in the CYTORONABSOLUTE® Flow Cytometer were adjusted to optimize hybridization-mediated fluorescence detection. Cluster analysis was used to determine the mean-peak channel fluorescence, since it allows thresholds of both fluorescence and another parameter (e.g., forward scattering or right scattering) to be preset, therefore permitting uniform criteria to be applied to different samples being analyzed. This procedure eliminates background noise resulting from particles presenting highly scattered fluorescence channel values.

In one embodiment, a method is provided for authenticating a sample by determining the presence of a target nucleic acid, the method comprising:

receiving a sample to be authenticated, wherein the sample has associated therewith an authentication code comprising one or more target nucleic acids, wherein the target nucleic acid is immobilized onto a microparticle, and wherein the microparticle comprises one or both of at least one unique first reporter compound and at least one discretely measurable electromagnetic radiation property;

contacting the microparticle with an oligonucleotide probe comprising a nucleic acid sequence complementary to at least a portion of the target nucleic acid and a second reporter compound capable of producing a detectable signal distinguishable from the first reporter compound upon formation of a duplex heterodimer of the target nucleic acid and the complementary oligonucleotide probe;

detecting the detectable signal associated with each of the uniquely identifiable microparticles; and identifying the sample as being authenticated by determining the presence of the authentication code based on the detectable signal being associated with each of the microparticles present in the authentication code.

In the method for authenticating a sample, the second reporter compound can comprise an optical label, a fluorescent dye, a radionucleotide, or an enzyme capable of producing the detectable signal upon intercalation in the duplex heterodimer.

In the method for authenticating a sample, the second reporter compound can comprise a fluorophore covalently attached to the oligonucleotide probe such that the detectable signal is a fluorescence signal detectable upon formation of the duplex heterodimer.

In the method for authenticating a sample, the authentication code can comprise at least two target nucleic acids.

In the method for authenticating a sample, each microparticle can comprise one or both of at least two unique first reporter compounds and at least two discretely measurable electromagnetic radiation properties.

In the method for authenticating a sample, the authentication code can comprise at least two target nucleic acids and each microparticle can comprise one or both of at least two unique first reporter compounds and at least two discretely measurable electromagnetic radiation properties.

In the method for authenticating a sample, detecting the detectable signal associated with each of the uniquely identifiable microparticles can be carried out by laser flow cytometry, laser scanning, or fluorescence microscopy, and combinations thereof.

In the method for authenticating a sample, the target nucleic acid can be incorporated into the formulation of the sample.

In the method for authenticating a sample, the sample can comprise a biological specimen, a pharmaceutical, a food, or a nutraceutical.

In the method for authenticating a sample, the target nucleic acid can be designed to be dissimilar from naturally occurring nucleotides. The target nucleic acid can comprise at least one stop codon. The target nucleic acid can comprises at least one stop codon in each of the three reading frames.

In the method for authenticating a sample, the authentication code can comprise one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The authentication code can consist of one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a method is provided for marking a sample for authentication, the method comprising: associating an authentication code comprising one or more target nucleic acids with a sample to be authenticated, wherein the target nucleic acid is immobilized onto a microparticle, and wherein the microparticle comprises one or both of at least one unique first reporter compound and at least one discretely measurable electromagnetic radiation property, such that detection of the target nucleic acid associated with each of the uniquely identifiable microparticles allows for authentication of the sample.

In the method for marking a sample for authentication, the target nucleic acid can be incorporated into the formulation of the sample.

In the method for marking a sample for authentication, the sample can comprise a biological specimen, a pharmaceutical, a food, or a nutraceutical.

In the method for marking a sample for authentication, the target nucleic acid can be designed to be dissimilar from naturally occurring nucleotides.

In the method for marking a sample for authentication, the target nucleic acid can comprise at least one stop codon.

In the method for marking a sample for authentication, the authentication code can comprise one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The authentication code can consist of one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, an isolated nucleic acid is provided comprising a sequence as set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, an isolated nucleic acid is provided selected from the group consisting of: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a method is provided for authenticating a sample by determining the presence of at least one target nucleic acid, the method comprising:

receiving a sample to be authenticated, wherein the sample comprises an associated authentication code comprising one or more target nucleic acids;

contacting the target nucleic acid with:
i) a dye that fluoresces when the dye intercalates in dsDNA, and
ii) a substrate comprising an immobilized oligonucleotide probe complementary to at least a portion of the corresponding target nucleic acid;
determining fluorescence associated with the substrate, wherein the fluorescence is caused by the dye intercalating in the dsDNA formed by the duplex heterodimer of the target nucleic acid and the complementary oligonucleotide probe; and
identifying the sample as being authenticated by determining the presence of the authentication code based on the fluorescence thereby associated with the substrate.

In one embodiment, a method is provided for authenticating a sample by determining the presence of at least one target nucleic acid, the method comprising:
receiving a sample to be authenticated, wherein the sample comprises an associated authentication code comprising one or more target nucleic acids;
contacting the target nucleic acid with a substrate comprising an immobilized oligonucleotide probe complementary to at least a portion of the target nucleic acid and a second reporter compound capable of producing a detectable signal upon formation of a duplex heterodimer of the target nucleic acid and the complementary oligonucleotide probe;
detecting the detectable signal associated with the substrate; and
identifying the sample as being authenticated by determining the presence of the authentication code based on the detectable signal associated with the substrate.

In the method for authenticating a sample, the second reporter compound can comprise an optical label, a fluorescent dye, a radionucleotide, or an enzyme capable of producing the detectable signal upon intercalation in the duplex heterodimer.

In the method for authenticating a sample, the second reporter compound can comprise a fluorophore covalently attached to either the oligonucleotide probe or the substrate such that the detectable signal is a fluorescence signal detectable upon formation of the duplex heterodimer.

In the method for authenticating a sample, the substrate can comprise a microparticle.

In the method for authenticating a sample, the authentication code can comprise at least two target nucleic acids, and each microparticle can comprise one or both of at least one unique first reporter compound and at least one discretely measurable electromagnetic radiation property.

In the method for authenticating a sample, the authentication code can comprise at least two target nucleic acids and each microparticle can comprise one or both of at least two unique first reporter compounds and at least two discretely measurable electromagnetic radiation properties.

In the method for authenticating a sample, the authentication code can comprises two or more target nucleic acids, and the target nucleic acids can be present at a known ratio other than 1:1.

In the method for authenticating a sample, the substrate can comprise an array having the oligonucleotide probe attached to a solid support at a known location.

In the method for authenticating a sample, detecting the detectable signal associated with each of the uniquely identifiable microparticles can be carried out by laser flow cytometry, laser scanning, or fluorescence microscopy, and combinations thereof.

In the method for authenticating a sample, the target nucleic acid can be incorporated into the formulation of the sample.

In the method for authenticating a sample, the sample can comprise a biological specimen, a pharmaceutical, a food, or a nutraceutical.

In the method for authenticating a sample, the target nucleic acid can be designed to be dissimilar from naturally occurring nucleotides.

In the method for authenticating a sample, the target nucleic acid can comprise at least one stop codon. In the method for authenticating a sample, the target nucleic acid can comprise at least one stop codon in each of the three possible reading frames.

In the method for authenticating a sample, the method can further comprise amplifying the target nucleic acid comprised within the authentication code.

In the method for authenticating a sample, the authentication code can comprise one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The authentication code can consist of one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a method is provided for marking a sample for authentication, the method comprising incorporating into the formulation of a sample to be authenticated an authentication code comprising one or more target nucleic acids designed to be dissimilar from naturally occurring nucleotides and comprising at least one stop codon, such that detection of the target nucleic acid allows for authentication of the sample.

In the method for marking a sample for authentication, the sample can comprise a biological specimen, a pharmaceutical, a food, or a nutraceutical.

In the method for marking a sample for authentication, the authentication code can comprise one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The authentication code can consist of one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a method is provided for authenticating an article by determining the presence of at least two target nucleic acids, the method comprising:
receiving an article to be authenticated, wherein the article comprises an authentication code comprising at least two target nucleic acids at a discernible location on the article;
contacting the authentication code on the article with: at least two oligonucleotide probes each comprising a nucleic acid sequence complementary to at least a portion of one of the target nucleic acids and a second reporter compound capable of producing a detectable signal upon formation of a duplex heterodimer of the target nucleic acid and the complementary oligonucleotide probe;
detecting the detectable signal associated with the authentication code as a result of formation of the duplex heterodimer of the target nucleic acid and the complementary oligonucleotide probe; and identifying the sample as being authenticated by determining the presence of the authentication code based on the detectable signal associated therewith.

In the method for authenticating an article by determining the presence of at least two target nucleic acids, the at least two oligonucleotide probes and the second reporter compound can be contacted with the authentication code by application with a marking pen having the oligonucleotide probes and the second reporter compound contained within. The second reporter compound can comprise an optical label, a fluorescent dye, a radionucleotide, or an enzyme capable of producing the detectable signal upon intercalation in the duplex heterodimer. The second reporter compound can comprise a fluorophore covalently attached to each of the at least two oligonucleotide probes such that the detectable signal is a fluorescence signal detectable upon formation of the duplex heterodimer.

In the method for authenticating an article, the authentication code can comprise each of the at least two target nucleic acids immobilized at a discrete location on the article and immobilized in one or both of a morphologically distinct shape and a distinct size. The morphologically distinct shape can consist of characters selected from letters A-Z and numbers 0-9.

In the method for authenticating an article by determining the presence of at least two target nucleic acids, the target nucleic acid can be designed to be dissimilar from naturally occurring nucleotides. The target nucleic acid can comprise at least one stop codon. The stop codon can be present in each of three possible reading frames.

In the method for authenticating an article by determining the presence of at least two target nucleic acids, the authentication code can comprise one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The authentication code can consist of one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment a method is provided for marking an article for authentication, the method comprising: immobilizing an authentication code on an article to be authenticated, the authentication code comprising at least two target nucleic acids at two discrete locations on the article and in one or both of a morphologically distinct shape and a distinct size, such that detection of the target nucleic acids allows for authentication of the sample.

In the method for marking an article for authentication, the morphologically distinct shape can consist of characters selected from letters A-Z and numbers 0-9.

In the method for marking an article for authentication, the target nucleic acid can be designed to be dissimilar from naturally occurring nucleotides. The target nucleic acid can comprise at least one stop codon. The stop codon can be comprised in each of three possible reading frames.

In the method for marking an article for authentication, the authentication code can comprise one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The authentication code can consist of one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a method is provided for authenticating a sample by determining the presence of at least one target nucleic acid, the method comprising:

receiving a sample to be authenticated, wherein the sample comprises an authentication code comprising at least one target nucleic acid;

contacting the target nucleic acid with a microparticle comprising an oligonucleotide probe complementary to at least a portion of the target nucleic acid and a second reporter compound capable of producing a detectable signal upon formation of a duplex heterodimer of the target nucleic acid and the complementary oligonucleotide probe;

incubating the target nucleic acid and the microparticle in the presence of an endonuclease such that single stranded nucleic acid can be digested;

detecting the detectable signal associated with the microparticle; and identifying the sample as being authenticated by determining the presence of the authentication code based on the detectable signal associated the microparticle.

In the method for authenticating a sample, the second reporter compound can comprise an optical label, a fluorescent dye, a radionucleotide, or an enzyme capable of producing the detectable signal upon intercalation in the duplex heterodimer. The second reporter compound can comprise a fluorophore covalently attached to either the oligonucleotide probe or the microparticle such that the detectable signal is a fluorescence signal detectable upon formation of the duplex heterodimer.

In the method for authenticating a sample, the authentication code can comprise at least two target nucleic acids, and each microparticle can comprise one or both of at least one unique first reporter compound and at least one discretely measurable electromagnetic radiation property.

In the method for authenticating a sample, the authentication code can comprises at least two target nucleic acids and each microparticle can comprise one or both of at least two unique first reporter compounds and at least two discretely measurable electromagnetic radiation properties.

In the method for authenticating a sample, the authentication code can comprise two or more target nucleic acids, and the target nucleic acids can be present at a known ratio other than 1:1.

In the method for authenticating a sample, detecting the detectable signal associated with each of the uniquely identifiable microparticles can be carried out by laser flow cytometry, laser scanning, or fluorescence microscopy, and combinations thereof.

In the method for authenticating a sample, the target nucleic acid can be incorporated into the formulation of the sample.

In the method for authenticating a sample, the sample can comprise a biological specimen, a pharmaceutical, a food, or a nutraceutical.

In the method for authenticating a sample, the target nucleic acid can be designed to be dissimilar from naturally occurring nucleotides. The target nucleic acid can comprise at least one stop codon. The stop codon can be in each of the three possible reading frames.

In the method for authenticating a sample, the method can further comprise amplifying the target nucleic acid comprised within the authentication code.

In the method for authenticating a sample, the authentication code can comprise one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The authentication code can consist of one or a combination of target nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment a kit is provided for authentication of a sample having an authentication code comprising at least one target nucleic acid, the kit comprising:

at least one oligonucleotide probe corresponding to the at least one target nucleic acid, wherein the oligonucleotide probe is complementary to at least a portion of the target nucleic acid, wherein the target nucleic acid is immobilized onto a microparticle, and wherein the microparticle comprises one or both of at least one unique first reporter compound and at least one discretely measurable electromagnetic radiation property;

a second reporter compound capable of producing a detectable signal upon formation of a duplex heterodimer of the target nucleic acid and the complementary oligonucleotide probe; and instructions for detecting the detectable signal associated with each of the uniquely identifiable microparticles and identifying the sample as being authenticated by determining the presence of the authentication code based on the detectable signal being associated with each of the microparticles present in the authentication code.

In the kit for authentication of a sample, the second reporter compound can comprise an optical label, a fluorescent dye, a radionucleotide, or an enzyme capable of producing the detectable signal upon intercalation in the duplex heterodimer. The second reporter compound can comprise a fluorophore covalently attached to the oligonucleotide probe such that the detectable signal is a fluorescence signal detectable upon formation of the duplex heterodimer.

In the kit for authentication of a sample, the authentication code can comprise two or more target nucleic acids. The target nucleic acid can be incorporated into the formulation of the sample. The sample can comprise a biological specimen, a pharmaceutical, a food, or a nutraceutical. The target nucleic acid can comprise at least one stop codon. The stop codon can be in each of the three possible reading frames.

In the kit for authentication of a sample, the oligonucleotide probe can comprise a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The oligonucleotide probe can consist of a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment a kit is provided for marking a sample for authentication, the kit comprising:

one or more target nucleic acids, wherein the target nucleic acid is immobilized onto a microparticle, and wherein the microparticle comprises one or both of at least one unique first reporter compound and at least one discretely measurable electromagnetic radiation property; and instructions for associating the target nucleic acid with a sample to be marked for authentication, such that detection of the target nucleic acid associated with each of the uniquely identifiable microparticles allows for authentication of the sample.

In the kit for marking a sample for authentication, the target nucleic acid can be incorporated into the formulation of the sample. The sample can comprise a biological specimen, a pharmaceutical, a food, or a nutraceutical.

In the kit for marking a sample for authentication, the target nucleic acid can be designed to be dissimilar from naturally occurring nucleotides. The target nucleic acid can comprise at least one stop codon. The stop codon can be in each of the three possible reading frames. The target nucleic acid can comprise one or a combination of nucleic acids set forth in: SEQ ID NO:

7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The target nucleic acid can consist of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a kit is provided for authentication of a sample having an authentication code comprising at least one target nucleic acid, the kit comprising:

a substrate comprising at least one immobilized oligonucleotide probe complementary to at least a portion of the at least one target nucleic acid;

a second reporter compound capable of producing a detectable signal upon formation of a duplex heterodimer of the target nucleic acid and the complementary oligonucleotide probe; and instructions for detecting the detectable signal associated with the substrate and identifying the sample as being authenticated by determining the presence of the authentication code based on the detectable signal associated with the substrate.

In the kit for authentication of a sample, the second reporter compound can comprise an optical label, a fluorescent dye, a radionucleotide, or an enzyme capable of producing the detectable signal upon intercalation in the duplex heterodimer. The second reporter compound can comprise a fluorophore covalently attached to either the oligonucleotide probe or the substrate such that the detectable signal is a fluorescence signal detectable upon formation of the duplex heterodimer.

In the kit for authentication of a sample, the substrate can comprise a microparticle. The substrate can comprise an array having the oligonucleotide probe attached to a solid support at a known location.

In the kit for authentication of a sample, the authentication code can comprise two or more target nucleic acids, and each microparticle can comprise one or both of at least one unique first reporter compound and at least one discretely measurable electromagnetic radiation property. The authentication code can comprise two or more target nucleic acids, and each microparticle can comprise one or both of at least two unique first reporter compounds and at least two discretely measurable electromagnetic radiation properties. In the kit for authentication of a sample, the target nucleic acid can be incorporated into the formulation of the sample. The sample can comprise a biological specimen, a pharmaceutical, a food, or a nutraceutical.

In the kit for authentication of a sample, the kit can further comprise primers for amplifying the target nucleic acid.

In the kit for authentication of a sample, the oligonucleotide probe can comprise a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The oligonucleotide probe can consist of a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a kit is provided for authenticating an article having an authentication code comprising at least two target nucleic acids at a discernible location on the article, the kit comprising:

at least two oligonucleotide probes each comprising a nucleic acid sequence complementary to at least a portion of one of the target nucleic acids;

a second reporter compound capable of producing a detectable signal upon formation of a duplex heterodimer of the target nucleic acid and the complementary oligonucleotide probe; and instructions for detecting the detectable signal associated with the authentication code as a result of formation of the duplex heterodimer of the target nucleic acid and the complementary oligonucleotide probe and identifying the sample as being authenticated by determining the presence of the authentication code based on the detectable signal associated therewith.

In the kit for authenticating an article, the at least two oligonucleotide probes and the second reporter compound can be contained within a marking pen. The second reporter compound can comprise a fluorescent dye capable of producing the detectable signal upon intercalation in the duplex heterodimer. The second reporter compound can comprise a fluorophore covalently attached to each of the at least two oligonucleotide probes such that the detectable signal is a fluorescence signal detectable upon formation of the duplex heterodimer.

In the kit for authenticating an article, the oligonucleotide probe can comprise a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The oligonucleotide probe can consist of a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a kit is provided for authenticating a sample having an authentication code comprising one or more target nucleic acids, the kit comprising:

a microparticle comprising an oligonucleotide probe complementary to at least a portion of a target nucleic acid;

a second reporter compound capable of producing a detectable signal upon formation of a duplex heterodimer of the target nucleic acid and the complementary oligonucleotide probe;

an endonuclease; and instructions for incubating the target nucleic acid and the microparticle in the presence of the endonuclease such that single stranded nucleic acid can be digested, detecting the detectable signal associated with the microparticle, and identifying the sample as being authenticated by determining the presence of the authentication code based on the detectable signal associated the microparticle.

In the kit for authenticating an article, the second reporter compound can comprise a fluorescent dye, a radionucleotide, or an enzyme capable of producing the detectable signal upon intercalation in the duplex heterodimer. The second reporter compound can comprise a fluorophore covalently attached to either the oligonucleotide probe or the microparticle such that the detectable signal is a fluorescence signal detectable upon formation of the duplex heterodimer.

In the kit for authenticating an article, the authentication code can comprise two or more target nucleic acids, and each microparticle can comprise one or both of at least one unique first reporter compound and at least one discretely measurable electromagnetic radiation property. The authentication code can comprise two or more target nucleic acids, and each microparticle can comprise one or both of at least two unique first reporter compounds and at least two discretely measurable electromagnetic radiation properties.

In the kit for authenticating an article, the target nucleic acid can be incorporated into the formulation of the sample. The sample can comprise a biological specimen, a pharmaceutical, a food, or a nutraceutical.

In the kit for authenticating an article, the kit can further comprise primers for amplifying the target nucleic acid.

In the kit for authenticating an article, the oligonucleotide probe can comprise a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The oligonucleotide probe can consist of a nucleic acid complementary to at least a portion of one or a combination of nucleic acids set forth in: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment, a marking pen is provided for authentication of an article having an authentication code on a surface thereof comprising one or more target nucleic acids, the marking pen comprising:

at least two oligonucleotide probes, each comprising a nucleic acid sequence complementary to at least a portion of one of the target nucleic acids; and a second reporter compound capable of producing a detectable signal upon formation of a duplex heterodimer of the target nucleic acid and the complementary oligonucleotide probe.

In the marking pen for authentication of an article, the second reporter compound can comprise a fluorescent dye capable of producing the detectable signal upon intercalation in the duplex heterodimer. The second reporter compound can comprise a fluorophore covalently attached to each of the at least two oligonucleotide probes such that the detectable signal is a fluorescence signal detectable upon formation of the duplex heterodimer.

The examples presented below utilize DNA as target nucleic acid. This is for illustrative purposes only. Wherever necessary, the methods of the present disclosure can be adapted readily for RNA targets, as would be known to the skilled practitioner. The following examples are offered by way of illustration and not by way of limitation.

Example 1

Detection of Target DNA Hybridized to Particle-Immobilized Oligonucleotide: DNA Binding Fluorophores Fluorophores that bind to dsDNA were used to detect hybridized target DNA. The target DNA in this example (SEQ ID NO: 2) was hybridized to bead-immobilized probe (SEQ ID NO: 1) in the presence of excess calf thymus DNA. Fluorophore was combined with hybridized target-bead suspension and analyzed by flow cytometry. Results are illustrated in FIGS. 2A-F using thiazole orange as the dsDNA binding fluorophore. The forward-angle scattering (FW-SC)×right-angle scattering (RT-SC) pattern of beads incubated with 1 μg calf thymus DNA in the absence (FIG. 2A) and presence (FIG. 2B) of target DNA is shown. Light-scatter gating of the beads by means of an image analysis software algorithm allows the analysis of select particles within a narrow range of FW-SC×RT-SC values, thus, eliminating particles outside the size range. The gated group of particles has the FW-SC×Green Fluorescence (GR-FL) pattern illustrated in FIG. 2, C and D, with thiazole orange as the dsDNA binding fluorophore, where further gating selects for the events used to calculate a mean channel fluorescence value. The group of particles selected in FIG. 2, C and D is represented in a fluorescence histogram in FIG. 2, E and F, where it can be seen that the distribution averages of a negative control (no target DNA) and positive (1000 fmoles of target) are clearly separated. Table 1 below shows the mean-peak channel fluorescence (MCF) for seven different fluorophores in the presence of CTDNA with and without added target DNA. Hybridizations were performed in a mixture containing $4\times10^4$ beads comprising oligonucleotide probe (SEQ ID NO: 1) immobilized thereto, with or without target (SEQ ID NO: 2, 1000 fmoles) in presence of 1 microgram of CTDNA and 0.15M potassium chloride, 0.01M Tris, and 1 mM (EDTA), pH 8.3, in a final volume of 10 microliters. The DNA was denatured at 96° C. for 3 minutes and hybridized at 65° C.

TABLE 1

| Fluorophore | MCF no target | MCF 1000 fmoles target |
|---|---|---|
| Thiazole Orange | 22.5 | 87.4 |
| Picogreen | 27.1 | 103.7 |
| Sybrgreen | 15.8 | 51.5 |
| TO-PRO-1 | 19.3 | 101.6 |
| TOTO-1 | 13 | 49.1 |
| YO-PRO-1 | 20.6 | 59.8 |
| YOYO-1 | 36 | 63.6 |
| Phycoerythrin | 21.5 | 34.7 |

There is no need to separate the particles associated with hybridized target and oligonucleotide from DNA free in solution as light-scatter gating of the particles by image analysis software allows analysis of a select group of those particles that present a cohesive, narrow range of forward angle scattering×right angle scattering values; limiting the analysis to only those particles of interest.

Example 2

Nuclease Protection

Hybridization of biotinylated particle-immobilized oligonucleotide probes (Oligo-1A) to target oligonucleotide (SEQ ID NO: 2) protected the probe from hydrolysis by single strand specific DNA endonuclease. As in Example 1, particle-immobilized oligonucleotide and CTDNA were incubated together in the presence and absence of 1000 femtomoles of target DNA, followed by incubation with S1 nuclease. Biotin was released upon endonuclease hydrolysis of the oligonucleotide probe unless it was protected from hydrolysis by hybridization with target DNA.

An 8 microliter aliquot of streptavidin-linked fluorophore (streptavidin-phycoerythrin from Molecular Probes), diluted 1:10 in TE buffer, was added to 16 microliters of nuclease-treated sample, and incubated for 10 minutes at room temperature. Binding of streptavidin-linked fluorophore served as reporter for intact bead-linked oligonucleotide. The mixture was analyzed using flow cytometry. The mean channel fluorescence of phycoerythrin without target was 21.5, with 1000 femtomoles of target it was 34.7.

Example 3

Quantification of Target DNA: DNA Binding Fluorophore

Figure 3:
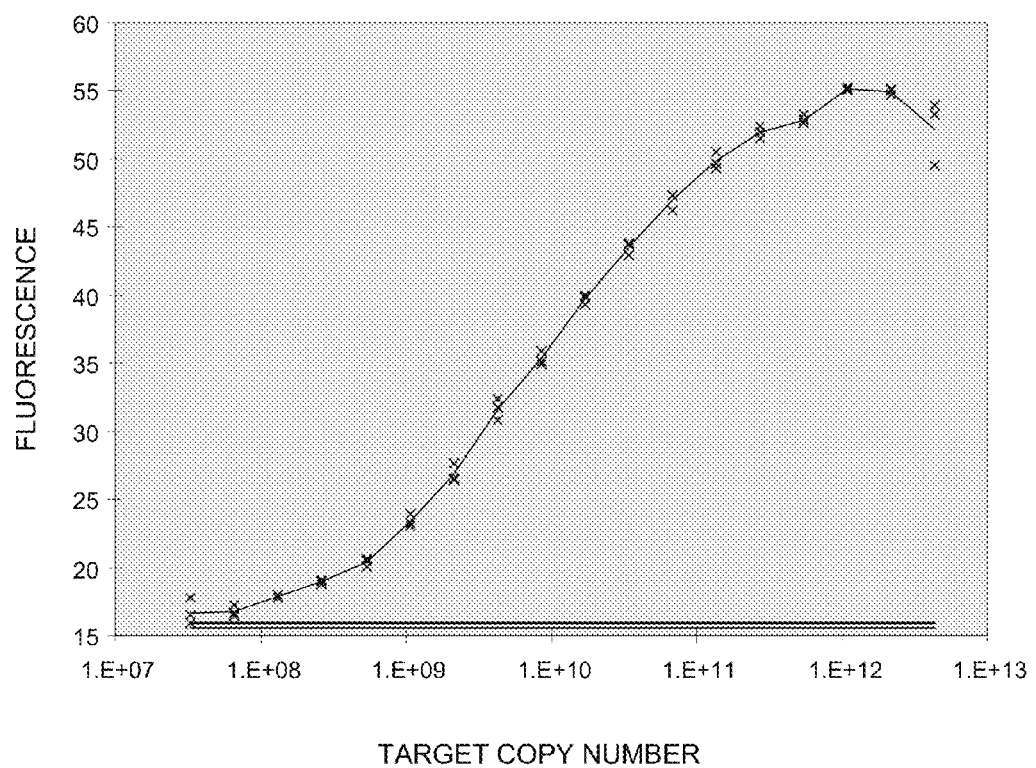
FIG. 3 is a plot of the mean green fluorescence vs copy number of double-strand target DNA.

The fluorescence of the fluorophore, sybr green, bound to the hybrid of target DNA (SEQ ID NO: 2) and bead-immobilized oligonucleotide (SEQ ID NO: 1) is shown as a function of the copy number of the target in FIG. 3.

The fluorescence signal associated with bead-immobilized oligonucleotide is monotonically dependent on the concentration, demonstrating the ability to quantitatively determine the amount of target DNA over a concentration range of about 6 orders of magnitude. As little as 25.7 picograms of target dsDNA corresponding to 440 attomoles, or about $2.5\times10^8$ copies of the 90-mer target, was clearly detected in a background of 0.8 μg non-specific calf thymus DNA. Thus the target DNA was readily detectable in the presence of about a $3.11\times10^4$-fold excess of non-specific DNA. The results also show that the method is very sensitive over the concentration range; a two-fold increase in target DNA concentration was readily detectable within a concentration range between about $1.25\times10^8$ to $1.09\times10^{12}$ copies of the target in a volume of 8 microliters. The average fluorescence obtained with thiazole orange, TOPRO-1, TOTO-1, YOPRO-1, YOYO-1, and picogreen, in each case, was also proportional to the concentration of the target DNA (data not shown).

Example 4

Quantification of Target DNA: dsDNA Binding Fluorophore

In an alternative embodiment, a soluble, biotinylated oligonucleotide probe was allowed to hybridize to its target DNA in solution. The target DNA-biotin-oligonucleotide probe hybrid was then allowed to bind to streptavidin-beads. To the suspension was then added 500 microliters of a 1:200 dilution of picogreen and incubated 2 min at room temperature. The suspension was introduced into the flow cytometer. The calculated particle-associated mean channel fluorescence was proportional to the concentration of target DNA in the sample (data not shown).

Example 5

Quantification of Target DNA: Nuclease Protection

Figure 4:
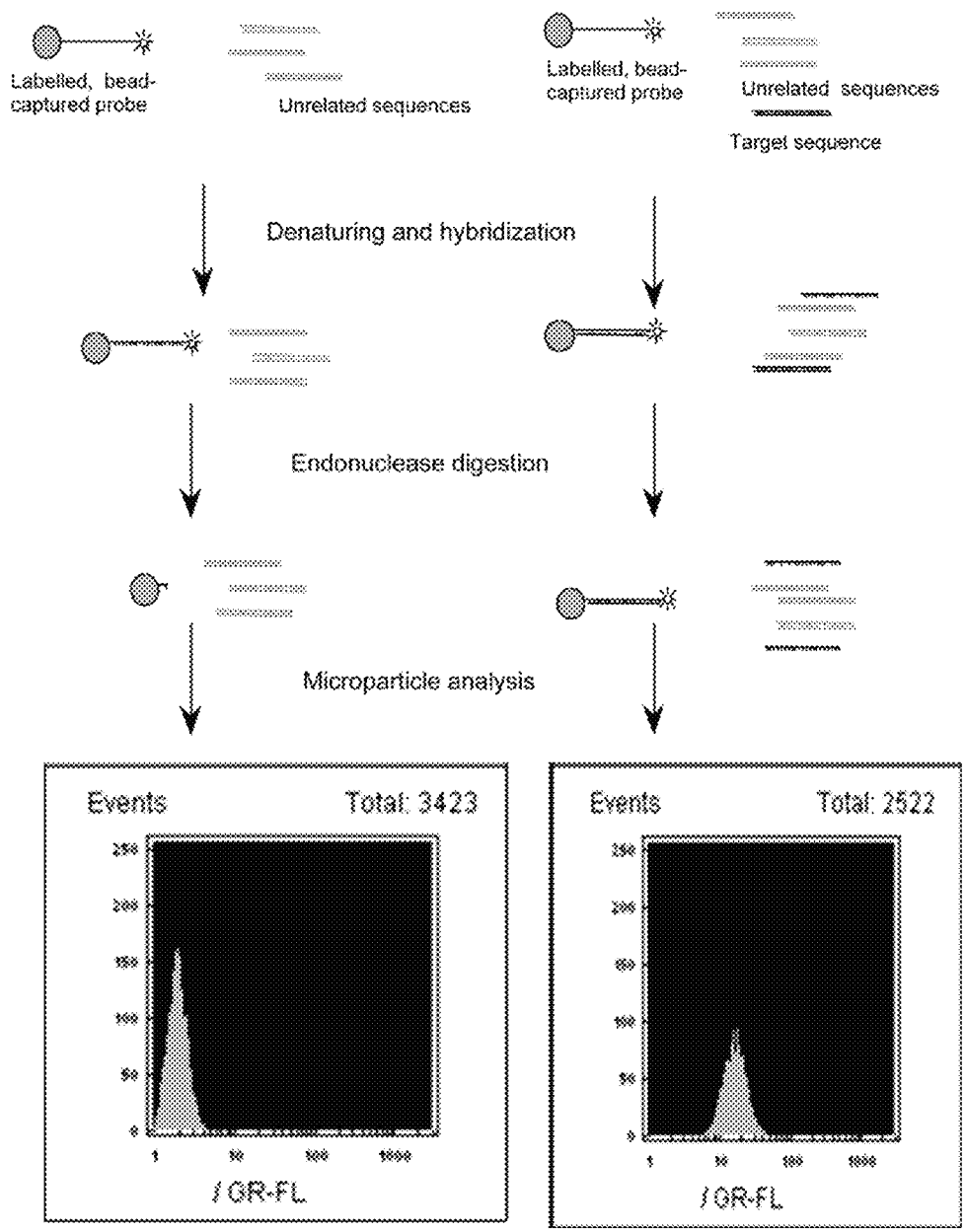
FIG. 4 shows a schematic of nuclease protection and detection of particle-associated target nucleic acid.

FIG. 4 shows a schematic of a nuclease protection-based assay for detection of particle-associated target nucleic acid.

Figure 5:
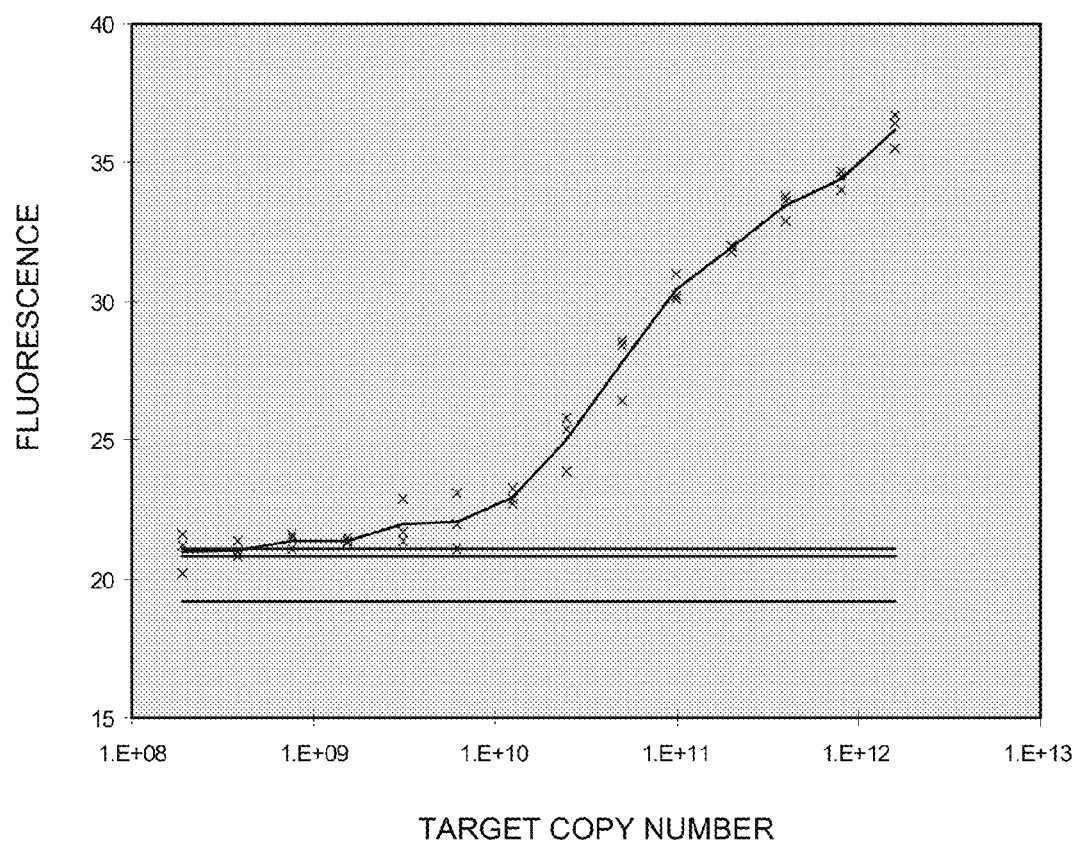
FIG. 5 is a plot of mean channel orange fluorescence (stained with streptavidin-conjugated R-phycoerythrin, nuclease protected dsDNA captured on beads) vs copy number of double-strand target DNA.

Protection of oligonucleotide probe from nuclease S1 digestion was proportional to the amount of target DNA. FIG. 5 shows the average fluorescence signal as a function of increasing single-stranded target DNA concentration. As little as 40.96 femtomoles (about $2.5\times10^{10}$ copies) of the 90 base-pair DNA target (SEQ ID NO: 2) was detected in about a 100-fold excess of non-target CTDNA.

Example 6

Detection of PCR Amplification Products: DNA Binding Fluorophore

To quantitatively measure low-abundance nucleic acids, PCR amplification of target DNA is frequently monitored as a function of amplification cycle number; the number of amplification cycles required to detect product being proportional to the target copy number.

In this example, 10 copies of target DNA were amplified from a plasmid-cloned DNA insert (SEQ ID NO. 3) using PCR. Target DNA (10 copies, SEQ ID NO: 3) was amplified in a volume of 100 microliters of an admixture containing CT (calf thymus) DNA, 5 micromolar NaOH, 4 milimolar $MgCl_2$, 18 mM Tris buffer, 54 mM KCl, 0.4 mM each primer (SEQ ID NO: 4 and SEQ ID NO: 5), 0.3 mM each dNTP, 0.108 microgram/microliter gelatin, 0.725 mM EDTA, 40 micromolar DTT, 9.5% glycerol, 0.02% Tween 20, 0.02% Nonidet P40.

Target DNA

The target DNA having the following sequence consisted of a DNA fragment cloned in pUC18:

```
SEQ ID NO: 3:
5'-CTGCAGGCGC CAGCGTGGAC CATCAAGTAG TAATGAACGC

ACGGACGAGG ACATCATAGA GATTACACCT TTATCCACAG

TTCTCGGTCT AACGCAGCAG TCAGTGTATC AGCACCAGCA

TCCGTAGTGA GTCTTCAGTG TCTGCTCCAG GATCGTGGCG

CTGCAG-3'
```

The underlined sequences correspond to the region amplified from the target DNA using the PCR primers described below (SEQ ID NO: 4 AND SEQ ID NO: 5).

PCR Primers

Primers used for target DNA amplification were synthetically prepared oligonucleotides according to the sequences:

```
SEQ ID NO: 4: (forward primer)
5'-CGCCAGCGTG GACCATCAAG TAGTAA-3'

SEQ ID NO: 5: (reverse primer)
5-'CACGATCCTG GAGCAGACAC TGAAGA-3'
```

PCR was carried out using standard thermal cycling protocols (cycles 1-5: 30 s at 96° C.: 60 s at 68° C.; cycles 6-40: 15 s at 96° C.; 60 s at 68° C.), terminating the reactions after either 5, 10, 15, 20, 25, 30, 35, and 40 cycles in the Perkin Elmer 9600 PCR System Thermocycler.

Hybridization

After amplification, 10 μL of the PCR admixture were combined with 10 microliters of a suspension containing about $10^5$ 3.5 micron diameter particles (Bangs Labs, Fishers, Ind.), previously coupled to the oligonucleotide probe (SEQ ID NO: 6) suspended in 2× hybridization buffer (0.3M potassium chloride, 0.02M Tris and 2 mM EDTA, pH 8.3), and the mixture was then heated for 3 minutes at 96° C., then allowed to cool to 65° C. and incubated for ten minutes.

Microparticle-Immobilized DNA Probe

The oligonucleotide probe immobilized on the particle has the sequence:

```
SEQ ID NO: 6:
5'-CTGCGTTAGA CCGAGAACTG TGGATAAAGG-3'
```

SEQ ID NO: 6: was modified by covalent attachment of biotin to the 3' terminus. The probe was allowed to bind to streptavidin-coated particles, 3.5 micrometer in diameter (Bangs Laboratories) using standard protocols.

DNA Staining

DNA staining was carried out by combining 500 μL of a 1:200 dilution of concentrated picogreen fluorescent dye with 20 μL of bead suspension comprising hybridized target and incubating the suspension for a minimum of 2 minutes at room temperature. Samples were next analyzed with the CYTORONABSOLUTE® flow cytometer.

Results

Figure 6:
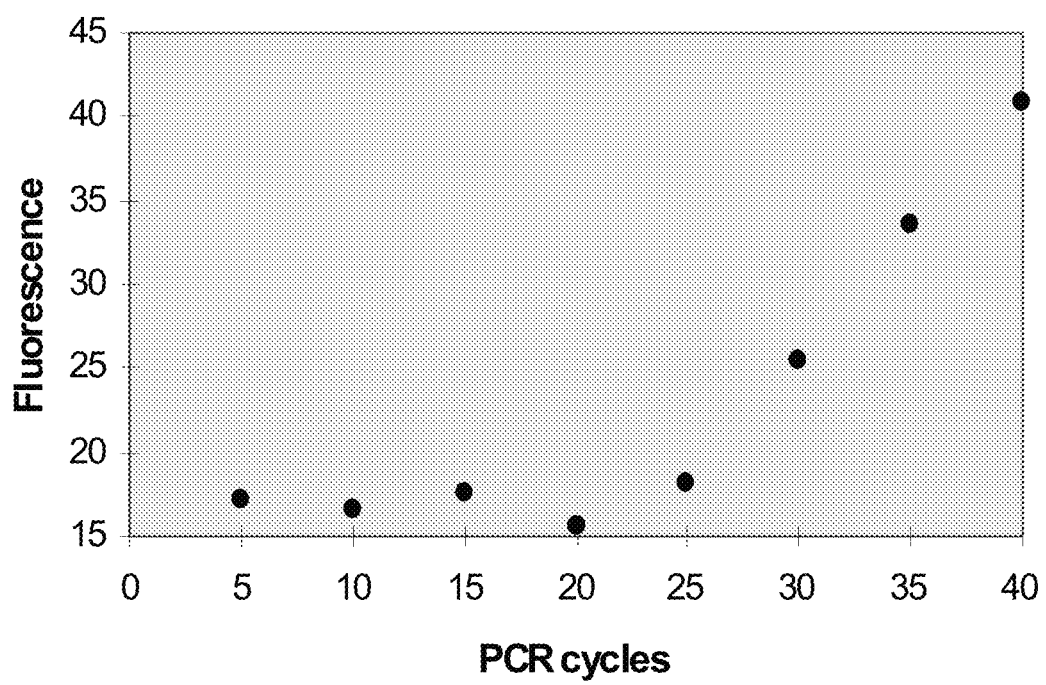
FIG. 6 is a plot of mean channel fluorescence vs PCR amplification cycle number.

PCR product was measured as mean channel fluorescence derived from picogreen bound to hybridized target and particle-immobilized oligonucleotide dsDNA. In FIG. 6, it can be seen that the mean channel fluorescence increased with increasing PCR cycle number after 30 cycles demonstrating quantitative detection of PCR amplification product.

Example 7

Laser Scanning Cytometry

Laser scanning cytometry can be used in practicing the present disclosure. In a laser scanning cytometer, such as the Compucyte Laser Scanning Cytometer, an optical detector moves past substances dispersed, usually uniformly, on a surface in two spatial dimensions, for instance, on the surface of a microscope slide. This differs from flow microfluorimetry wherein particles move past a detector in one dimension (substantially one at a time in a moving stream).

Particles comprising a target-specific oligonucleotide probe must be large enough to be resolved by the detection system used in the laser scanning cytometer. Particles are preferably greater than or equal to about 0.3 microns, more preferably between about 1 to about 5 microns. The particles, sample comprising target nucleic acid and a compound that produces a detectable fluorescence when bound to dsDNA are combined to form a mixture. The mixture is diluted sufficiently to allow uniform dispersion of the particles on a microscope slide. The laser scanner moves over the slide and uses light scattering and/or fluorescence of the particles to trigger measurement of detectable fluorescence from a compound that is bound to hybridized target and particle-immobilized oligonucleotide. The laser scanning cytometer differentiates a plurality of distinct target-specific particles by the specific light scattering and/or fluorescence characteristics of the target-specific particles.

Example 8

DNA Arrays

In laser scanning cytometry and flow microfluorimetry, analyte detection relies on spatial resolution. In flow cytometry, resolution is one dimension. In laser scanning cytometry resolution is in two dimensions.

A DNA chip comprising oligonucleotide arrays represents a two-dimensional separation device. Methods for preparing such arrays are described in International Patent Application Publication No. WO 9818961 and in the U.S. Patents noted in the Background section.

In operation, a range of measurements, x1, is made in one direction, the x direction, and a range of measurements, y1, is made in a direction orthogonal to x, the y direction. Events detected as x1y1 are known to be associated with a particular target-specific probe. Similarly, x2y2 measurements are known to be associated with a probe for the same target or for a different target, and so on.

DNA chips or slides comprising oligonucleotide arrays can be prepared by depositing and anchoring oligonucleotides directly to the surface or indirectly through chemical linkers or other immobilizing agents, all using techniques known in the art and found in International Patent Application Publication No. WO 9818961, as well as the U.S. Patents noted heretofore. They are immobilized in discrete xy locations on one surface of a chip or slide. Each xy locus, or spot, is specific for any desired target nucleic acid. Multiple spots specific to a single target can be located on the chip or slide to effect assay replication (replicate spots). Any desired number of target-specific spots and replicate spots can be used. Preferably, the chip or slide comprises between about 5 to about 20 target-specific spots and about the same number of replicate spots, more preferably the chip or slide comprises between about 100 to about 1000 target-specific spots and 10 to 100 replicate spots for each target. The DNA chip or slide is contacted with sample, and a compound that produces a detectable fluorescence signal when bound to dsDNA. The target-correlated fluorescence originating from the spots, that is, each specific xy location on the chip or slide is measured, for example, using a laser scanning device. The fluorescence signal is related to the presence or amount of the specific target nucleic acid.

In particular, a DNA chip having about 100 target-specific loci and about 10 replicate loci to SEQ ID NO. 1, which oligonucleotide sequences are printed on silylated slides (CEL Associates). The print spots are about 125 μm in diameter and are spaced 300 μm apart from center to center. About 10 replicate probes to irrelevant sequence (for example, probes to plant genes where mammalian sequences are detected) are also printed on the slides. Printed glass slides are treated with sodium borohydrate solution (0.066M NaBH4, 0.06M Na AC) to ensure amino-linkage of probes to the slides. The slides are then boiled in water for 2 minutes to denature the cDNA. A biological containing from about 30 to about 30,000 target nucleic molecules is heated to 99° C. for 5 minutes, then pre-cooled before hybridization, in this case, held at room temperature for 5 minutes, and then applied to the slides. The slides are covered with glass cover slips, sealed with DPX (Fluka) and hybridized at 60° C. for 4-6 hours. At the end of hybridization slides are cooled to room temperature. The slides are washed in 1×SSC, 0.2% SDS at 55° C. for 5 minutes, 0.1×SSC, 0.2% SDS at 55° C. for 5 minutes. The slides are stained by contacting the entire surface with a 1:200 dilution of concentrated picogreen fluorescent dye and incubating for a minimum of 2 minutes at room temperature. After a quick rinse in 0.1×SSC, 0.2% SDS, the slides are air-blown dried and ready for scanning Arrays are scanned for picogreen dye fluorescence using the ScanArray 3000 (General Scanning, Inc.). ImaGene Software (Biodiscovery, Inc.) is subsequently used for quantitation. The intensity of each spot is corrected by subtracting the immediate surrounding background.

The fluorescent signal is related to the presence or amount of the specific target nucleic acid and the slide has performed 10 replicates of this assay with mean of fluorescence from replicate test spots compared using statistical methods to mean of fluorescence from replicate probes to irrelevant sequence.

The above methods and procedures are repeated using a DNA chip having about 100 target-specific loci and about 10 replicate loci to SEQ ID NO. 1, SEQ ID NO. 2, SEQ ID NO. 3, SEQ ID NO 4, SEQ ID NO. 5, and SEQ ID NO.6.

Example 9

Detection of PCR Amplification Products: Homogeneous Method

The purpose of this Example is to perform PCR thermocycling with IPC-IP beads in the PCR mix. Addition of DNA stain follows thermocycling.

The materials and procedures of Example 6 are employed, using the conditions, primers and probes identified below. Target DNA (10 copies), SEQ ID NO. 3, is amplified in a volume of 100 microliters using suitable PCR protocols that includes components of a PCR admixture, 0.25 microliter of $10^5$ oligonucleotide-bound 1.7 micron beads. Beads used are poly[styrene-co(p-vinylbenzylthio)proprionic acid] 95:5 molar ratio beads prepared as described in U.S. Pat. Nos. 5,149,737; 5,210,289 and 5,278,267, and the appropriate concentration of a DNA-binding fluorophore, in this case, 500 microliter of a 1:200 dilution of concentrated picogreen, which is added following the thermocycling. Amplification reactions are set up in PCR conditions of Example 6, except $10^5$ oligonucleotide-bound microparticles is included in the admixture and a temperature cycle allowing for hybridization after the PCR cycles is added. The presence of the amplified target DNA in the resulting mixture is then determined by flow cytometry using, for example, the CYTORONABSOLUTE® flow cytometer.

Target DNA

A target DNA having the following sequence is cloned in pUC18:

```
SEQ ID NO. 3:
5'-CTGCAGGCGC CAGCGTGGAC CATCAAGTAG TAATGAACGC

ACGGACGAGG ACATCATAGA GATTACACCT TTATCCACAG

TTCTCGGTCT AACGCAGCAG TCAGTGTATC AGCACCAGCA

TCCGTAGTGA GTCTTCAGTG TCTGCTCCAG GATCGTGGCG

CTGCAG-3'
```

Amplification and Hybridization Reactions

Using PCR conditions and primers identified below, the sequences underlined in SEQ ID NO. 3: are amplified using modified amplification protocols (cycles 1-5: 30 s at 96° C.: 60 s at 68° C.; cycles 6-40: 15 s at 96° C.; 60 s at 68° C.; cycle 41: 5 minutes at 72° C.; cycle 42: 3 minutes at 96° C.; cycle 43: 60 s at 50° C.) in the PE9600 Thermocycler.

```
SEQ ID NO. 4: (forward primer)
5'-CGCCAGCGT GGACCATCA AGTAGTAA-3'

SEQ ID NO. 5: (reverse primer)
5-'CACGATCCT GGAGCAGAC ACTGAAGA-3'
```

The oligonucleotide probe immobilized on the particle has the sequence:

SEQ ID NO. 6:
5'-CTGCGTTAG ACCGAGAAC TGTGGATAA AGG-3'

SEQ ID NO. 6: is modified by covalent attachment to the surface of polystyrene particles, 1 micrometer in diameter using standard protocols.

DNA Staining

DNA staining is carried out by combining 500 µL of a 1:200 dilution of concentrated picogreen with 20 µL of the above-identified PCR bead suspension comprising hybridized amplified target, and incubating the suspension for a minimum of 2 minutes at room temperature Results PCR product is measured as mean channel fluorescence derived from picogreen bound to hybridized target and particle-immobilized oligonucleotide dsDNA.

Example 10

Detection of PCR Amplification Products: Homogeneous Method

The purpose of this Example is to perform PCR thermocycling with beads and DNA dye in the PCR mix. The materials and procedures of Example 9 are employed except that 2.5 microliters of concentrated thermostable dye (for example, SYBR Green I dye, Molecular Probes, Eugene, Oreg.) is added to the PCR suspension containing target, prior to thermocycling. Other thermostable dyes that can be used include ethidium bromide and propidium iodide.

Results

PCR product is measured as mean channel fluorescence derived from SYBR Green bound to hybridized target and particle-immobilized oligonucleotide dsDNA.

Example 11

Detection of PCR Amplification Products: Homogeneous Method

The purpose of this Example is to perform PCR thermocycling in the presence of thermostable DNA dye in the PCR mix. Addition of microbeads follows thermocycling.

The materials and procedures of Example 9 are employed with 2.5 microliters of a concentrated thermostable SYBR Green dye added to the PCR target suspension prior to thermocycling. Other thermostable dyes that can be used include ethidium bromide and propidium iodide.

DNA Hybridization

Following thermocycling, 10 microliters of $10^5$ oligonucleotide-bound microparticles (1 to 10 microns in size) suspended in 2× hybridization buffer (0.3M potassium chloride, 0.02M Tris and 2 mM EDTA, pH 8.3), are added to 10 microliters of the amplified product-dye admixture, and heated for 3 minutes at 96° C., then allowed to cool to 65° C. to allow hybridization.

Analysis

The hybridized samples are supplemented with 500 µL of 1 mM Tris, 10 mM EDTA buffer and analyzed with for example, the CYTORONABSOLUTE® flow cytometer.

Results

PCR product is measured as mean channel fluorescence derived from SYBR Green bound to hybridized target and particle-immobilized oligonucleotide dsDNA.

Example 12

Detection of Immobilized Target DNA Hybridized to Oligonucleotide with Detection Via DNA Binding Fluorophores In this example, an article is identified or authenticated by immobilizing target DNA to the article, simultaneously contacting the article with both a complementary oligonucleotide and a compound which is capable of binding to duplex nucleic acid and which upon binding or being bound thereto is capable of producing a detectable signal. In this example, a marking pen is used to deliver both complementary oligonucleotide and an intercalating dye.

A target DNA (Target 1) comprises SEQ ID NO. 1, as follows:

5'-TTTCCAAGTA AGCAATAACG TCAGCTCTTT CTTGTGGCTT

CTTCATACCA GCGAAAGACA TCTTAGTACC TGGCATGAAC

TTCTTTGGGT-3'.

Target 1 is associated with the surface of an article using the method of Okamato, et al. ("Microarray fabrication with covalent attachment of DNA using Bubble Jet technology", Nature Biotechnology 18, 438-441 (2000)). Articles are printed in a 10×10 array of possible locations such that the locations used are in the shape of the letters "A", "T", "C", or "G".

A detector oligonucleotide (Detector 1) comprises SEQ ID NO: 2, as follows:

5'-ACCCAAAGAA GTTCATGCCA GGTACTAAGA TGTCTTTCGC

TGGTATGAAG AAGCCACAAG AAAGAGCTGA CGTTATTGCT

TTGGAAA-3'.

Target 1 is detected using a marking pen that delivers Detector 1 and approximately 0.5 µM intercalating dye selected from the list of Thiazole Orange, Picogreen, Sybrgreen, TO-PRO-1, YO-PRO1, or YOYO-1. For each article to be authenticated, the pen delivers approximately 1 pmole of Detector 1 in the presence of 1 microgram of CTDNA and 0.15M potassium chloride, 0.01M Tris, and 1 mM (EDTA), pH 8.3, in an approximate volume of 10 µL, over the array area on the article.

Hybridization of Detector 1 to Target 1 is detected by illumination of the array area with an excitation wavelength of light matched to the dye selected, and visualized through an appropriate optical filter matched to the fluorescence of said dye, or preferably using a handheld reader designed to deliver said light and measure said fluorescence location-by-location within the array.

The skilled artisan recognizes that the methods of this example may use other DNA sequences for target and detector DNA, including DNA from natural sources, that other methods are suitable for both associating the target DNA with the article, and that the other methods are available for binding and detection of the intercalating dye to the target/detector heteroduplex. Additionally, the requirement for detector oligonucleotide to match target nucleic acid provides for "lock & key" assurance. Also, the present example illustrates that an additional level of assurance is created by the spatial information revealed.

Example 13

Detection of Target DNA Hybridized to Detector Oligonucleotide Immobilized to Signature Array Elements This example shows a method for authenticating an article by determining the presence of a code comprising at least two target nucleic acid sequences upon contacting the article with both a detector oligonucleotide and an intercalating dye. Further, in this example, the target DNA is associated with the article at discrete locations and in morphologically distinct shapes.

A target DNA (Target 2) comprises the same number of nucleotides as Target 1, but no sequence identity at any position. A detector oligonucleotide (Detector 2) is synthesized to comprise sequence complimentary to Target 2.

Target 1 and Target 2 are printed on articles for authentication by printing one or the other target DNA in each of two locations on the article (i.e., four possible combinations, as follows: Position 1=Target 1, Position 2=Target 1; Position 1=Target 1, Position 2=Target 2; Position 1=Target 2, Position 2=Target 1; and, Position 1=Target 2, Position 2=Target 2). For each group of articles to share the same code, one of the characters A-Z or numbers 0-9 is selected for each of two locations (36 combinations), and each character at each location is printed in one of 3 discernable sizes. The skilled artisan recognizes that this simple system yields 7776 possible codes from just two target DNA's.

Target 1 and/or Target 2 is detected using a marking pen that delivers complementary Detector DNA and approximately 0.5 μM intercalating dye as described in Example 1.

Example 14

Detection of Target DNA in Combination with a Signature Array Using Detector DNA and a DNA Binding Fluorophore Streptavidin Coated Polystyrene Particles, 0.5% w/v, are purchased from Spherotech, Inc., 1840 Industrial Dr., Suite 270, Libertyville, Ill. 60048. Target DNA of the above Example 2 is modified by linking biotin to the 5' terminus through two tetraethylene glycol (TEG-TEG) spacers with and without an aminodiol (ADL) linker at the 3' terminus for attachment to microparticles. To prepare the microparticles of each cluster, biotinylated target DNA is incubated at ambient temperature for 10 minutes with $5 \times 10^4$ beads per 10 μL in 0.15M potassium chloride, 0.01M tris(hydroxymethyl) aminomethane (Tris), 1 mM ethylenediaminetetraacetic acid (EDTA), pH 8.3, according to Table 2.

TABLE 2

| Cluster # | Particle Size | DNA |
|---|---|---|
| 1 | 0.3-0.39 μm | Target 1 |
| 2 | 0.4-0.6 μm | Target 1 |
| 3 | 0.7-0.9 μm | Target 1 |
| 4 | 1.5-1.9 μm | Target 1 |
| 5 | 2.0-2.9 μm | Target 1 |
| 6 | 3.0-3.9 μm | Target 1 |
| 7 | 4.0-4.9 μm | Target 1 |
| 8 | 5.0-5.9 μm | Target 1 |
| 9 | 6.0-8.0 μm | Target 1 |
| 10 | 8.0-13.9 μm | Target 1 |
| 11 | 14.0-17.9 μm | Target 1 |
| 12 | 18.0-23.0 μm | Target 1 |
| 13 | 0.3-0.39 μm | Target 2 |
| 14 | 0.4-0.6 μm | Target 2 |
| 15 | 0.7-0.9 μm | Target 2 |
| 16 | 1.5-1.9 μm | Target 2 |
| 17 | 2.0-2.9 μm | Target 2 |
| 18 | 3.0-3.9 μm | Target 2 |
| 19 | 4.0-4.9 μm | Target 2 |
| 20 | 5.0-5.9 μm | Target 2 |
| 21 | 6.0-8.0 μm | Target 2 |
| 22 | 8.0-13.9 μm | Target 2 |
| 23 | 14.0-17.9 μm | Target 2 |
| 24 | 18.0-23.0 μm | Target 2 |

In order to assure classification of the particles to the correct cluster, signature arrays are constructed of clusters that are comprised of alternating use of size range and Target DNA, according to Table 3 as follows:

TABLE 3

| Cluster # | Particle Size | Set 1 | Set 2 |
|---|---|---|---|
| 1 | 0.3-0.39 μm | None or 1X to 4X | None |
| 2 | 0.4-0.6 μm | None | None or 1X to 4X |
| 3 | 0.7-0.9 μm | None or 1X to 4X | None |
| 4 | 1.5-1.9 μm | None | None or 1X to 4X |
| 5 | 2.0-2.9 μm | None or 1X to 4X | None |
| 6 | 3.0-3.9 μm | None | None or 1X to 4X |
| 7 | 4.0-4.9 μm | None or 1X to 4X | None |
| 8 | 5.0-5.9 μm | None | None or 1X to 4X |
| 9 | 6.0-8.0 μm | None or 1X to 4X | None |
| 10 | 8.0-13.9 μm | None | None or 1X to 4X |
| 11 | 14.0-17.9 μm | None or 1X to 4X | None |
| 12 | 18.0-23.0 μm | None | None or 1X to 4X |
| 13 | 0.3-0.39 μm | None or 1X to 4X | None |
| 14 | 0.4-0.6 μm | None | None or 1X to 4X |
| 15 | 0.7-0.9 μm | None or 1X to 4X | None |
| 16 | 1.5-1.9 μm | None | None or 1X to 4X |
| 17 | 2.0-2.9 μm | None or 1X to 4X | None |
| 18 | 3.0-3.9 μm | None | None or 1X to 4X |
| 19 | 4.0-4.9 μm | None or 1X to 4X | None |
| 20 | 5.0-5.9 μm | None | None or 1X to 4X |
| 21 | 6.0-8.0 μm | None or 1X to 4X | None |
| 22 | 8.0-13.9 μm | None | None or 1X to 4X |
| 23 | 14.0-17.9 μm | None or 1X to 4X | None |
| 24 | 18.0-23.0 μm | None | None or 1X to 4X |

Thus, $10^{12}$ different signatures can be constructed from just these 12 different bead sets and 2 different target DNAs(!). Microparticles comprising clusters of a selected signature are associated with a liquid product. To detect the presence of said signature, the microparticles are concentrated by centrifugation, then mixed with detector DNA at a final suspension containing about $10^5$ particles per 10 μL in 0.3M potassium chloride, 0.02M Tris and 2 mM EDTA, pH 8.3. The mixture is then heated for 3 minutes at 96° C., then allowed to cool to 65° C. and incubated for ten minutes.

DNA staining is carried out by combining 500 μL of a 1:200 dilution of concentrated picogreen fluorescent dye with 20 μL of bead suspension comprising hybridized target and incubating the suspension for a minimum of 2 minutes at room temperature. Samples are analyzed with a flow cytometer. Thus, any measured fluorescence signal is generated from particle-immobilized target/detector DNA heteroduplex, and a signature array is revealed.

Example 15

Laser Scanning Cytometry

Laser scanning cytometry can be used in practicing the present disclosure. In a laser scanning cytometer, such as the Compucyte Laser Scanning Cytometer, an optical detector moves past substances dispersed, usually uniformly, on a surface in two spatial dimensions, for instance, on the surface of a microscope slide. This differs from flow microfluorimetry wherein particles move past a detector in one dimension (substantially one at a time in a moving stream).

Particles comprising a target-specific oligonucleotide probe must be large enough to be resolved by the detection system used in the laser scanning cytometer. Particles are preferably greater than or equal to about 0.3 microns, more preferably between about 1 to about 5 microns. The particles, sample comprising target nucleic acid and a compound that produces a detectable fluorescence when bound to dsDNA are combined to form a mixture. The mixture is diluted sufficiently to allow uniform dispersion of the particles on a microscope slide. The laser scanner moves over the slide and uses light scattering and/or fluorescence of the particles to trigger measurement of detectable fluorescence from a compound that is bound to hybridized target and particle-immobilized oligonucleotide. The laser scanning cytometer differentiates a plurality of distinct target-specific particles by the specific light scattering and/or fluorescence characteristics of the target-specific particles.

Example 16

Figure 9:
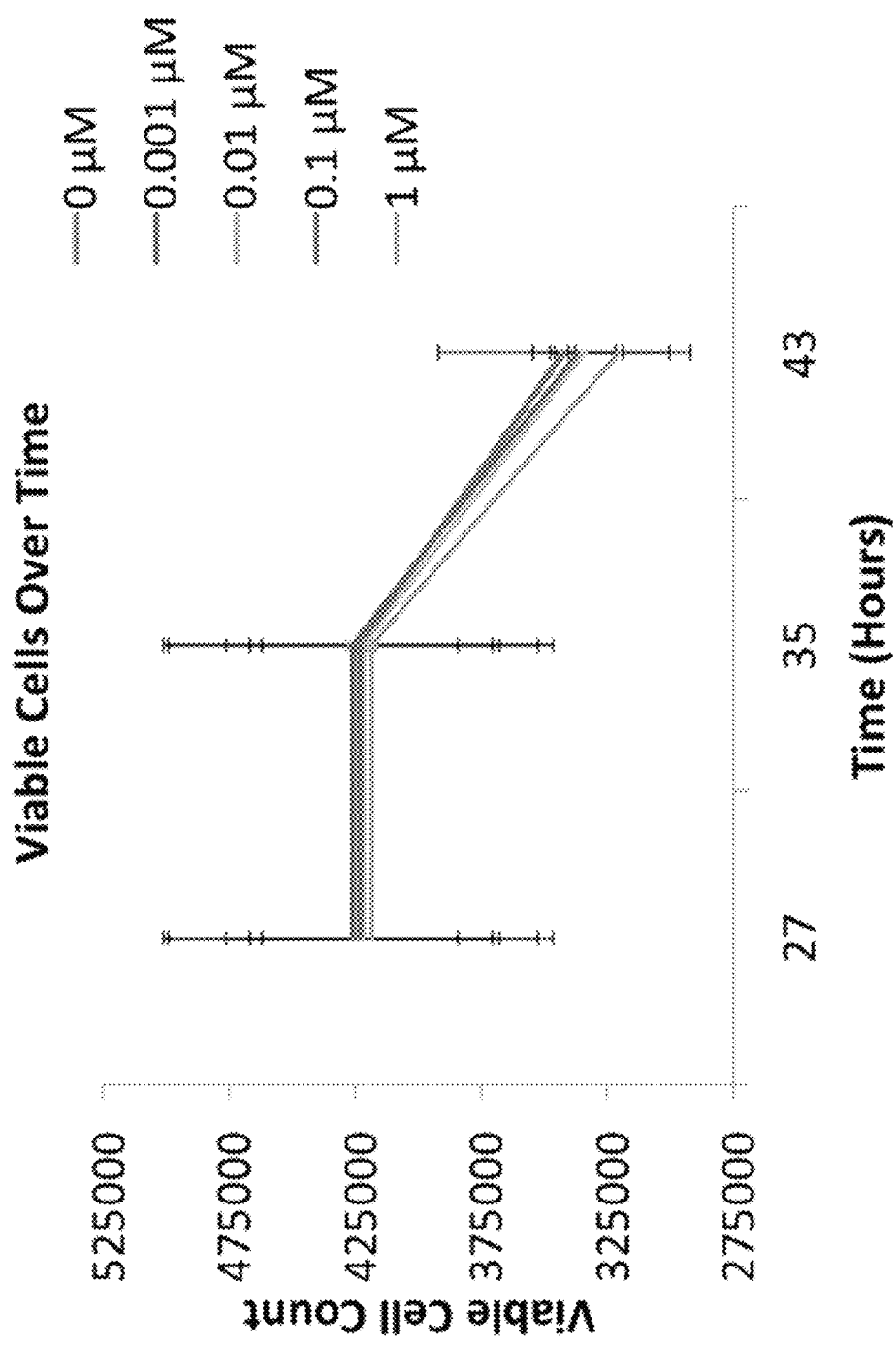
FIG. 9 is a plot of cell viability over time for fresh Wistar rat hepatocytes cultured with DNA tracer at various fixed concentration levels.

Quantification of Cellular Toxicity of DNA Sequences Having Minimized Similarity to Naturally Occurring DNA Sequences A DNA sequence representative of Sequence Set #1 was tested in order to perform an initial assessment of its cellular toxicity. Cellular toxicity of oligos was assessed by exposing fresh Wistar rat hepatocytes to predetermined concentrations of SEQ ID NO: 7 oligonucleotides. Cell viability was measured using alamarBlue® dye (Invitrogen) analyzed by microplate reader. SEQ ID NO: 7 concentrations tested (in triplicate) were: 0.001 μM, 0.01 μM, 0.1 μM, and 1 μM. Thus, oligo concentrations of up to 1000× the 1 nM concentration intended for use for product authentication were tested for signs of toxicity. FIG. 9 summarizes the preliminary cytotoxicity screen results. No significant differences exist between each concentration of SEQ ID NO: 7 and the control cell cultures. At time point 43 hours all cells, including the control, showed reduced viability; this decrease in viability is to be expected for fresh cell cultures, even under ideal environmental conditions.

Example 17

Persistent Identification of a Biological Specimen or Biologic Drug Through PCR Analysis The ability to identify a biological specimen at any point in the analytical process, from the time of collection to the time of results reporting, would be valuable to clinicians and patients. Likewise, the same is true for tracing a biologic drug through it distribution chain from manufacture to the patient. Nucleic acid tracers of the type identified herein are used to identify such a biological specimen or biologic drug when it is no longer associated with its corresponding identifying documentation or original container. In one embodiment, one or more tracer oligonucleotides is or are associated with a biological specimen at the time of specimen collection. In another embodiment, one or more tracer oligonucleotides is or are associated with a biologic drug at the time of specimen collection. The tracer oligonucleotides are associated with a particular identity. At a point after collection, the specimen can undergo clinically relevant analytical assays without interference from the tracer sequences having minimal overlap with known biological sequences. In addition, the identity of the specimen can be determined by performing analysis of the biological specimen using a detection method such as that described in Example 11.

In another embodiment, at least one tracer oligonucleotide is associated with the specimen at the time of collection for sample identification. At any point in the PCR amplification process, a portion of the specimen may be collected and tested for two or more nucleotide sequences: the tracer oligonucleotide and a nucleotide sequence occurring naturally within the PCR product. Detection of the tracer and PCR product oligonucleotides can be performed simultaneously using a number of methods; one such method is the use of complementary oligonucleotide sequences, each attached to distinct populations of microparticles. Detection is performed using the method described in Example 11.

Figure 10:
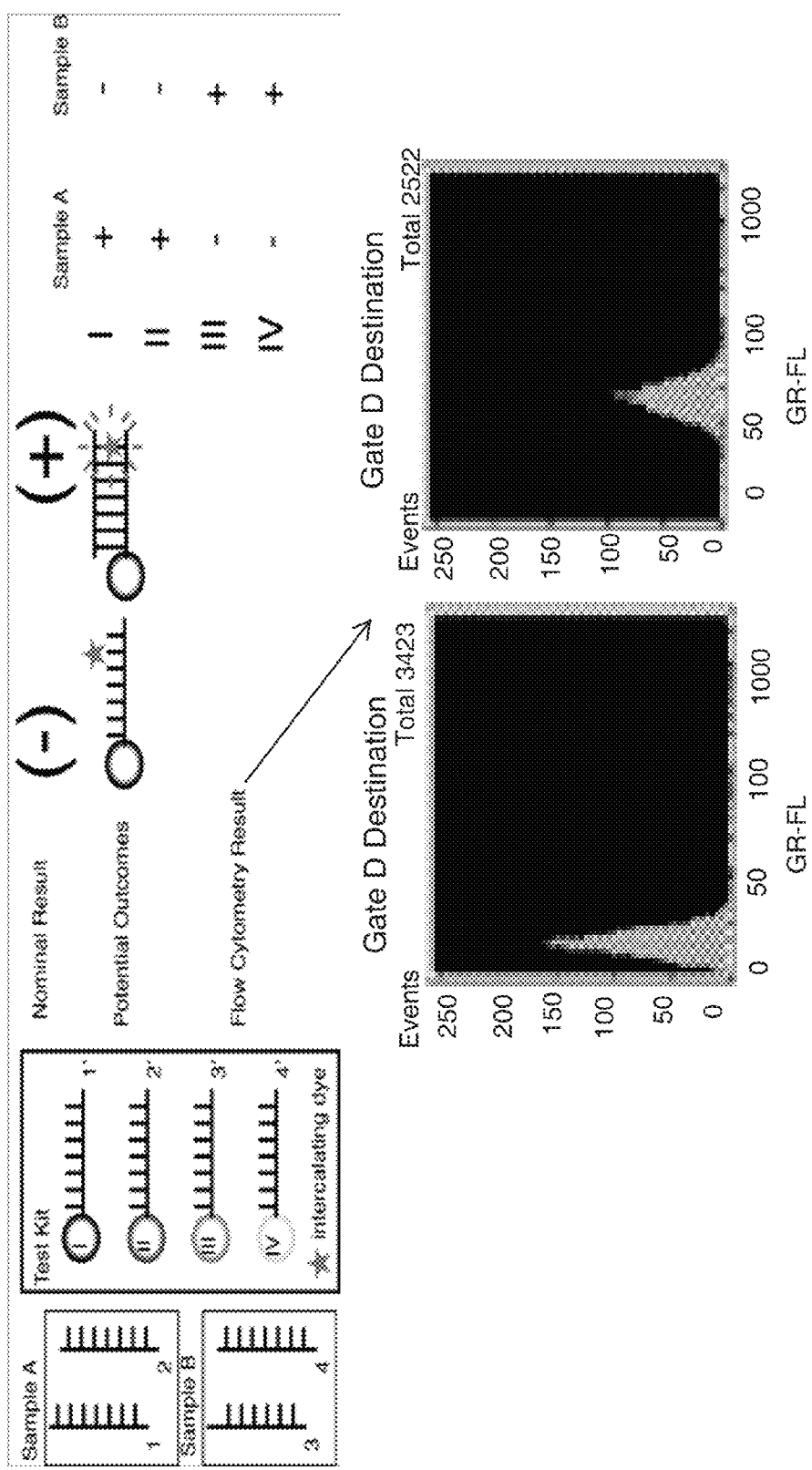
FIG. 10 shows a schematic of simultaneous detection of tracer oligonucleotide and PCR product.

FIG. 10 shows the method of simultaneous tracer and PCR product oligonucleotides. Tracer oligonucleotides are labeled 1 and 3, and PCR product oligonucleotides are labeled 2 and 4. The test kit comprises an intercalating dye and four populations of microspheres labeled with oligo complements 1', 2', 3', and 4'. When a sample is mixed with the test kit and heteroduplex nucleotide formation occurs, the intercalating dye emits a (+) fluorescence signal using flow cytometry for detection. Otherwise, the intercalating dye emits no significant (−) fluorescence signal. In this way, one can test for the presence of tracer and PCR product oligonucleotides simultaneously. Analysis of Sample A yields (+) for intercalating dye fluorescence for microparticles I and II, and (−) for microparticles III and IV. Analysis of Sample B yields (−) for intercalating dye fluorescence for microparticles I and II, and (+) for microparticles III and IV.

Example 18

Figure 11:
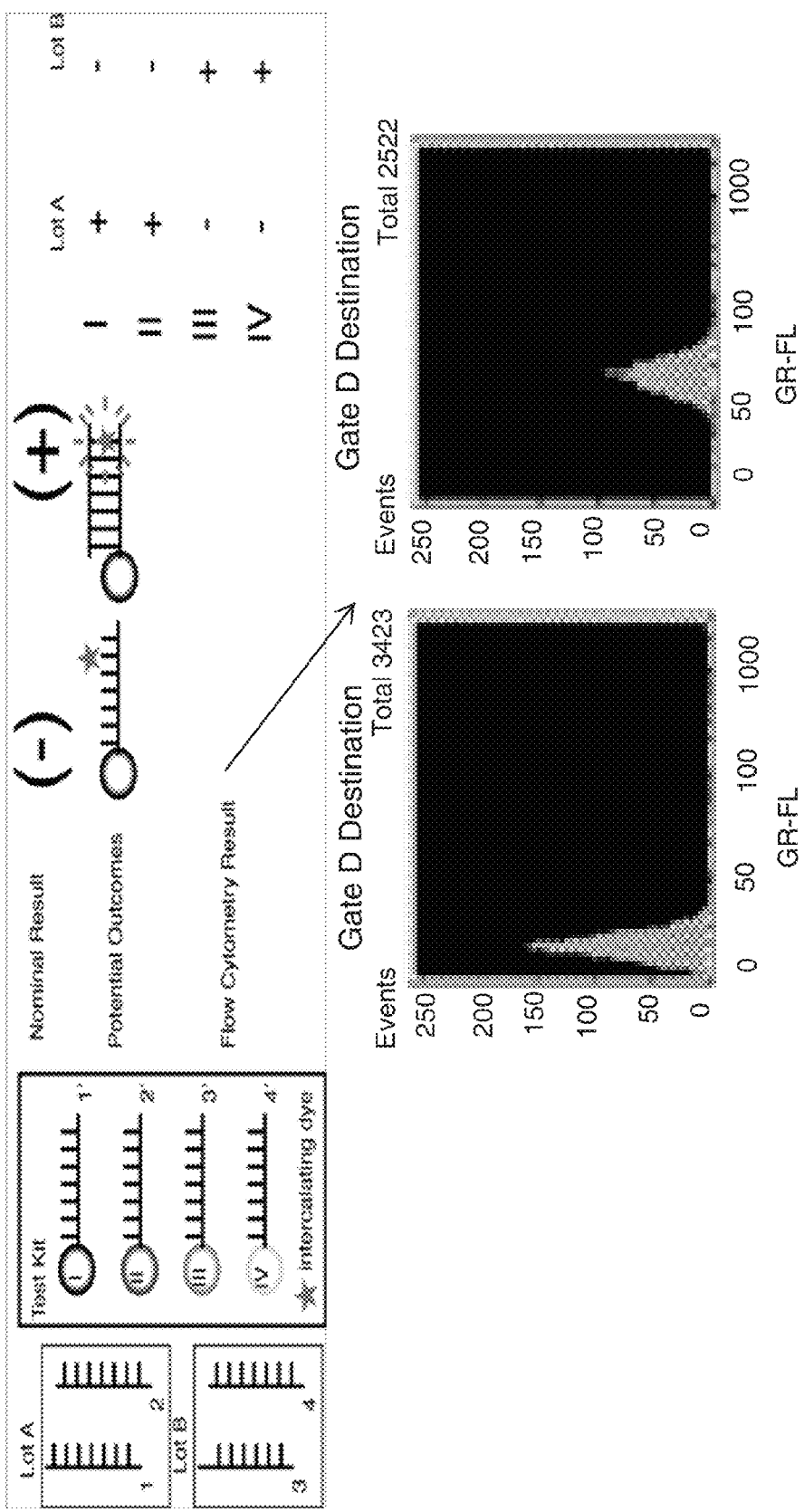
FIG. 11 shows a schematic of authentication of a liquid biological pharmaceutical.

Authentication of a Product Intended for Intimate or Parenteral Contact with Biological Organisms Using Nucleotide Sequences Designed for Enhanced Safety The present disclosure is used to incorporate one or more oligonucleotides with a material intended for use in intimate or parenteral contact with a biological organism. In one example, the product is a pharmaceutical intended for parenteral administration. Sets of ssDNA oligonucleotides (selected from among a panel of oligonucleotides meeting the requirements of Sequence Set #2) are added in trace amounts and in different combinations per drug lot. To test for the presence of the code, a sample of a single drug lot is mixed with a kit containing a dye that fluoresces when it intercalates in dsDNA and groups of microparticle containing distinguishable levels of a dye that fluoresces at a longer wavelength than the intercalating dye. Each group of microparticle type bears capture oligonucleotides that are complementary to those used for coding. To authenticate the biologic, a sample is combined with the test kit ingredients, heated to 96° C. for 3 minutes and hybridized at 65° C. The mixture is then analyzed using a flow cytometer. FIG. 11 shows the authentication process and exemplary results.

In one embodiment, the microparticles emit fluorescence at a wavelength according to the distinguishable level of dye associated with the microparticle. If a fluorescent microparticle also emits fluorescence at the intercalating dye wavelength, then the heterodimer is present and the corresponding target oligo was present in the drug lot. In this manner, specific target oligos can be identified as be present in a sample based on the fluorescence associated with the microparticle and the fluorescence associated with the intercalating dye. Thus, a specific lot can be identified using a small array of testing reagents. The test kit is capable of detecting very low concentrations of oligos; this detection method is capable of sensing oligo copy numbers as low as $1 \times 10^8$. It should be understood that other methods of identifying a microparticle may be used. For example, different size microparticles or microparticles comprising ligands for other types of reporting and/or targeting structures may be used.

In a further embodiment, increasing the number of unique oligos and microparticle types can increase the code complexity. In addition, one can increase code complexity by adding a third property: oligo ratios. For example, by simply combining the tracer oligos in ratios, 3 parts Oligo #1 to 1 part Oligo #2 the number of possible unique codes becomes very large.

The present disclosure has been described in detail in respect to particular preferred embodiments. It will be understood that variations and modifications can be effected without departing from the scope and spirit of the present disclosure. The entire contents of all cited patents, patent applications, and non-patent disclosures are expressly incorporated herein by reference.

We claim:

1. A method for authenticating a sample by determining the presence of at least one target nucleic acid, the method comprising:
   a) receiving a sample to be authenticated, wherein the sample comprises an associated authentication code comprising at least two target nucleic acids having a sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16;
   b) contacting the target nucleic acids with:
      a dye that fluoresces when the dye intercalates in dsDNA, and
      a microparticle comprising an oligonucleotide probe complementary to at least a portion of the target nucleic acid, wherein each microparticle comprises one or both of at least one unique first reporter compound and at least one discretely measurable electromagnetic radiation property;
   c) determining fluorescence associated with the microparticle, wherein the fluorescence is caused by the dye intercalating in the dsDNA formed by a duplex heterodimer of the target nucleic acid and the complementary oligonucleotide probe; and
   d) identifying the sample as being authenticated by determining the presence of the authentication code based on the fluorescence thereby associated with the microparticle.

2. The method of claim 1, wherein the target nucleic acids are incorporated into a formulation of the sample.

3. The method of claim 1, wherein the sample is selected from the group consisting of a biological specimen, a pharmaceutical, a food, and a nutraceutical.

4. The method of claim 1, wherein the microparticle further comprises a fluorescent compound capable of fluorescing at a different wavelength than the dye.

5. The method of claim 1, wherein the at least one unique first reporter compound comprises a fluorescence signal.

6. The method of claim 1, wherein the authentication code further comprises a known ratio other than 1:1 of the duplex heterodimers formed by a plurality of target nucleic acids and complementary oligonucleotide probes.

7. A method for authenticating a sample by determining the presence of at least one target nucleic acid, the method comprising:
   receiving a sample to be authenticated, wherein the sample comprises an associated authentication code comprising one or more target nucleic acids having a sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16;
   contacting the target nucleic acid with a substrate comprising an immobilized oligonucleotide probe complementary to at least a portion of the target nucleic acid and a second reporter compound capable of producing a detectable signal upon formation of a duplex heterodimer of the target nucleic acid and the complementary oligonucleotide probe;
   detecting the detectable signal associated with the substrate; and
   identifying the sample as being authenticated by determining the presence of the authentication code based on the detectable signal associated with the substrate.

8. The method of claim 7, wherein the second reporter compound comprises an optical label, a fluorescent dye, a radionucleotide, or an enzyme capable of producing the detectable signal upon intercalation in the duplex heterodimer.

9. The method of claim 7, wherein the second reporter compound comprises a fluorophore covalently attached to either the oligonucleotide probe or the substrate such that the detectable signal is a fluorescence signal detectable upon formation of the duplex heterodimer.

10. The method of claim 7, wherein the substrate comprises a microparticle.

11. The method of claim 10, wherein the authentication code comprises at least two target nucleic acids, and wherein each microparticle comprises one or both of at least one unique first reporter compound and at least one discretely measurable electromagnetic radiation property.

12. The method of claim 11, wherein detecting the detectable signal associated with each of the uniquely identifiable microparticles is carried out by laser flow cytometry, laser scanning, or fluorescence microscopy, and combinations thereof.

13. The method of claim 7, wherein the authentication code comprises two or more target nucleic acids, and wherein the target nucleic acids are present at a known ratio other than 1:1.

14. The method of claim 7, wherein the substrate comprises an array having the oligonucleotide probe attached to a solid support at a known location.

* * * * *